(12) United States Patent
Ek

(10) Patent No.: US 8,361,159 B2
(45) Date of Patent: Jan. 29, 2013

(54) SYSTEM FOR ARTICULAR SURFACE REPLACEMENT

(75) Inventor: Steven W. Ek, Bolton, MA (US)

(73) Assignee: Arthrosurface, Inc., Franklin, MA (US)

( * ) Notice: Subject to any disclaimer, the term of this patent is extended or adjusted under 35 U.S.C. 154(b) by 0 days.

(21) Appl. No.: 11/169,326

(22) Filed: Jun. 28, 2005

(65) Prior Publication Data

US 2006/0020343 A1    Jan. 26, 2006

Related U.S. Application Data

(63) Continuation-in-part of application No. 10/308,718, filed on Dec. 3, 2002, now Pat. No. 7,163,541, and a continuation-in-part of application No. 10/994,453, filed on Nov. 22, 2004, and a continuation-in-part of application No. 10/308,718, filed on Dec. 3, 2002, now Pat. No. 7,163,541.

(60) Provisional application No. 60/583,549, filed on Jun. 28, 2004, provisional application No. 60/523,810, filed on Nov. 20, 2003.

(51) Int. Cl.
*A61F 2/38* (2006.01)

(52) U.S. Cl. .................. 623/20.15; 623/20.22

(58) Field of Classification Search ............... 623/20.14, 623/20.17, 20.18, 20.32–20.34
See application file for complete search history.

(56) References Cited

U.S. PATENT DOCUMENTS

| | | |
|---|---|---|
| 992,819 A | 5/1911 | Springer |
| 1,451,610 A | 4/1923 | Gestas |
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 3,176,395 A | 4/1965 | Warner et al. |
| 3,715,763 A | 2/1973 | Link |
| 3,840,905 A | 10/1974 | Deane |
| 3,852,830 A | 12/1974 | Marmor |
| 4,016,651 A | 4/1977 | Kawahara et al. |
| 4,034,418 A | 7/1977 | Jackson et al. |
| 4,044,464 A | 8/1977 | Schiess et al. |
| 4,158,894 A | 6/1979 | Worrell |
| 4,319,577 A | 3/1982 | Bofinger et al. |
| 4,330,891 A | 5/1982 | Brånemark et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |

(Continued)

FOREIGN PATENT DOCUMENTS

| | | |
|---|---|---|
| AU | 2001262308 | 12/2001 |
| AU | 2001259327 B2 | 2/2005 |

(Continued)

OTHER PUBLICATIONS

International Search Report with Written Opinion dated Sep. 29, 2006 received in corresponding International Patent Application Serial No. PCT/US05/30120 (9 pages).

(Continued)

*Primary Examiner* — Andrew Yang
(74) *Attorney, Agent, or Firm* — Grossman Tucker Perreault & Pfleger PLLC

(57) ABSTRACT

A system for replacing a portion of an articular surface including providing an implant site and installing an implant into the implant site. The implant site includes a first and a second excision site which at least partially intersect with one another. Each of the first and second excision sites are formed by providing a respective axis and excising a portion of the articular surface relative to the respective axes.

21 Claims, 23 Drawing Sheets

U.S. PATENT DOCUMENTS

| | | |
|---|---|---|
| 4,531,517 A | 7/1985 | Forte et al. |
| 4,535,768 A | 8/1985 | Hourahane et al. |
| 4,565,768 A | 1/1986 | Nonogaki et al. |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,781,182 A | 11/1988 | Purnell et al. |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,920,958 A | 5/1990 | Walt et al. |
| 4,927,421 A | 5/1990 | Goble et al. |
| 4,938,778 A | 7/1990 | Ohyabu et al. |
| 4,940,467 A | 7/1990 | Tronzo |
| 4,945,904 A | 8/1990 | Bolton et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,053,049 A | 10/1991 | Campbell |
| 5,092,895 A | 3/1992 | Albrektsson et al. |
| 5,100,405 A | 3/1992 | McLaren |
| 5,127,920 A | 7/1992 | MacArthur |
| 5,154,720 A | 10/1992 | Trott et al. |
| 5,180,384 A | 1/1993 | Mikhail |
| 5,192,291 A | 3/1993 | Pannek, Jr. |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,313,382 A | 5/1994 | Goodfellow et al. |
| 5,314,478 A | 5/1994 | Oka et al. |
| 5,314,482 A | 5/1994 | Goodfellow et al. |
| 5,324,295 A | 6/1994 | Shapiro |
| 5,336,224 A | 8/1994 | Selman |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,401 A | 3/1995 | Bahler |
| 5,409,490 A | 4/1995 | Ethridge |
| 5,409,494 A | 4/1995 | Morgan |
| 5,413,608 A | 5/1995 | Keller |
| 5,423,822 A | 6/1995 | Hershberger |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,520,695 A | 5/1996 | Luckman |
| 5,522,900 A | 6/1996 | Hollister |
| 5,534,031 A | 7/1996 | Matsuzaki et al. |
| 5,540,696 A | 7/1996 | Booth, Jr. et al. |
| 5,580,353 A | 12/1996 | Mendes et al. |
| 5,591,170 A | 1/1997 | Spievack et al. |
| 5,593,450 A | 1/1997 | Scott et al. |
| 5,595,193 A | 1/1997 | Walus et al. |
| 5,601,550 A | 2/1997 | Esser |
| 5,607,480 A | 3/1997 | Beaty |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,465 A | 12/1997 | Burkinshaw |
| 5,702,467 A | 12/1997 | Gabriel et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| RE36,020 E | 12/1998 | Moore et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,286 A | 7/1999 | Ashby et al. |
| 5,964,752 A | 10/1999 | Stone |
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,045,564 A | 4/2000 | Walen |
| 6,052,909 A | 4/2000 | Gardner |
| 6,059,831 A | 5/2000 | Braslow |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,102,948 A | 8/2000 | Brosnahan, III |
| 6,120,511 A | 9/2000 | Chan |
| 6,120,542 A | 9/2000 | Camino et al. |
| 6,132,433 A | 10/2000 | Whelan |
| 6,146,385 A | 11/2000 | Torrie et al. |
| 6,149,654 A | 11/2000 | Lanny |
| 6,152,960 A | 11/2000 | Pappas |
| 6,159,216 A | 12/2000 | Burkinshaw et al. |
| 6,165,223 A | 12/2000 | Metzger et al. |

| | | |
|---|---|---|
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,217,549 B1 | 4/2001 | Selmon et al. |
| 6,217,619 B1 | 4/2001 | Keller |
| 6,235,060 B1 | 5/2001 | Kubein-Meesenburg |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,375,658 B1 | 4/2002 | Hangody et al. |
| 6,383,188 B2 | 5/2002 | Kuslich |
| 6,415,516 B1 | 7/2002 | Tirado et al. |
| 6,443,954 B1 | 9/2002 | Bramlet et al. |
| 6,461,373 B2 | 10/2002 | Wyman et al. |
| 6,468,309 B1 | 10/2002 | Lieberman |
| 6,478,178 B2 | 11/2002 | Ralph et al. |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,551,322 B1 | 4/2003 | Lieberman |
| 6,554,866 B1 | 4/2003 | Aicher et al. |
| 6,575,980 B1 | 6/2003 | Robie et al. |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,679,917 B2 | 1/2004 | Ek |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,884,246 B1 | 4/2005 | Sonnabend et al. |
| 6,884,621 B2 | 4/2005 | Liao et al. |
| 6,893,467 B1 | 5/2005 | Bercovy |
| 6,923,813 B2 | 8/2005 | Phillips et al. |
| 6,926,739 B1 | 8/2005 | Oconnor |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,204,839 B2 | 4/2007 | Dreyfuss |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augostino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,758,643 B2 | 7/2010 | Stone et al. |
| 7,806,872 B2 | 10/2010 | Ponzi |
| 7,815,645 B2 | 10/2010 | Haines |
| 7,828,853 B2 | 11/2010 | Ek et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,955,382 B2 | 6/2011 | Flanagan et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,137,406 B2 | 3/2012 | Novak et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,162,947 B2 | 4/2012 | Dreyfuss |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |

| | | |
|---|---|---|
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,298,247 B2 | 10/2012 | Sterrett et al. |
| 8,298,284 B2 | 10/2012 | Cassani |
| 8,308,662 B2 | 11/2012 | Lo |
| 8,308,732 B2 | 11/2012 | Millett et al. |
| 2001/0012967 A1 | 8/2001 | Mosseri |
| 2001/0034526 A1 | 10/2001 | Kuslich et al. |
| 2001/0039455 A1 | 11/2001 | Simon et al. |
| 2001/0056266 A1 | 12/2001 | Tallarida et al. |
| 2002/0049444 A1 | 4/2002 | Knox |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130665 A1 | 7/2003 | Pinczewski |
| 2003/0130741 A1 | 7/2003 | McMinn |
| 2003/0144736 A1 | 7/2003 | Sennett |
| 2003/0171756 A1 | 9/2003 | Fallin et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0082906 A1 | 4/2004 | Tallarida et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0154398 A1 | 7/2005 | Miniaci |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0251268 A1 | 11/2005 | Truncale |
| 2005/0287187 A1 | 12/2005 | Mansmann |
| 2006/0004461 A1 | 1/2006 | Justin et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058883 A1 | 3/2006 | Aram et al. |
| 2006/0085006 A1 | 4/2006 | Ek |
| 2006/0085077 A1 | 4/2006 | Cook et al. |
| 2006/0149370 A1 | 7/2006 | Schmieding et al. |
| 2006/0184187 A1 | 8/2006 | Surti |
| 2006/0190002 A1 | 8/2006 | Tallarida |
| 2006/0195112 A1 | 8/2006 | Ek |
| 2006/0229726 A1 | 10/2006 | Ek |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093890 A1 | 4/2007 | Eliasen et al. |
| 2007/0093896 A1 | 4/2007 | Malinin |
| 2007/0100447 A1 | 5/2007 | Steinberg |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0288803 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0086139 A1 | 4/2008 | Bourke et al. |
| 2008/0097618 A1 | 4/2008 | Baker et al. |
| 2008/0103506 A1 | 5/2008 | Volpi et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0208201 A1 | 8/2008 | Moindreau et al. |
| 2008/0275512 A1 | 11/2008 | Albertirio et al. |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0138077 A1 | 5/2009 | Weber et al. |
| 2009/0143783 A1 | 6/2009 | Dower |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216285 A1 | 8/2009 | Ek et al. |
| 2009/0222012 A1 | 9/2009 | Karnes et al. |
| 2009/0228105 A1 | 9/2009 | Son et al. |
| 2009/0234452 A1 | 9/2009 | Steiner et al. |
| 2009/0264889 A1 | 10/2009 | Long et al. |
| 2009/0264928 A1 | 10/2009 | Blain |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0092535 A1 | 4/2010 | Cook et al. |
| 2010/0112519 A1 | 5/2010 | Hall et al. |
| 2010/0256645 A1 | 10/2010 | Zajac et al. |
| 2010/0256758 A1 | 10/2010 | Gordon et al. |

| | | | |
|---|---|---|---|
| 2010/0268227 A1 | 10/2010 | Tong et al. |
| 2010/0268346 A1 | 10/2010 | Tong et al. |
| 2011/0009964 A1 | 1/2011 | Schwartz et al. |
| 2011/0059312 A1 | 3/2011 | Howling et al. |
| 2011/0066242 A1 | 3/2011 | Lu et al. |
| 2011/0125263 A1 | 5/2011 | Webster et al. |
| 2011/0152869 A1 | 6/2011 | Ek et al. |
| 2011/0196367 A1 | 8/2011 | Gallo |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0027837 A1 | 2/2012 | DeMuth et al. |
| 2012/0109136 A1 | 5/2012 | Bourque et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0150225 A1 | 6/2012 | Burkhart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0265298 A1 | 10/2012 | Schmieding et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| EP | 0241240 | 10/1987 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 9920192 | 4/1999 |
| WO | 0013597 | 3/2000 |
| WO | 0105336 | 1/2001 |
| WO | 0182677 | 11/2001 |
| WO | 0191648 | 12/2001 |
| WO | 0191672 | 12/2001 |
| WO | 0217821 | 3/2002 |
| WO | WO 02/086180 A2 | 10/2002 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 20050512331 | 6/2005 |
| WO | 2006004885 | 1/2006 |
| WO | 2006004885 | 8/2006 |

OTHER PUBLICATIONS

International Search Report with Written Opinion dated Nov. 29, 2006 received in corresponding International Patent Application Serial No. PCT/US05/23200 (7 pages).

International Preliminary Report on Patentability dated Mar. 1, 2007 received in corresponding International Patent Application No. PCT/US2005/030120 (6 pages).

ATOS News, Oct. 2005, "The Artificial Limb "Eclipse"—A new draft without shank in the implantation of artifici shoulder limbs", cover page w/pp. 40-41, with English translation dated Jan. 13, 2006 (2 pgs).

Article—"Arthroscopically Assisted Treatment of Tibial Plateau Fractures", Suganuma, Jun and Alcutsu, Seiji, The Journal of Arthroscopic and Related Surgery, vol. 20, No. 10, Dec. 2004, pp. 1084-1089.

EPO Search Report received in related EPO Application No. 03 02 6286.9 dated Apr. 27, 2004 (6 pgs).

M. Siguier, MD et al, "Preliminary Results of Partial Surface Replacement of the Femoral Head in Osteonecrosis", The Journal of Arthroplasty, vol. 14, No. 1, 1999, pp. 45-51.

T. Siguler, MD et al, "Partial Resurfacing Arthroplasty of the Femoral Head in Avascular Necrosis", Clinical Orthopaedics and Related Research, No. 386, 2001, pp. 85-92.

EPO Examination Report dated Feb. 22, 2005, received in related EPO Application No. 01 932 833.5 (3 pgs).

EPO Office Action dated Mar. 15, 2005, received in related EPO Application No. 03 026 286.9 (3 pgs).

Bale, MD, Reto J., et al, "Osteochondral Lesions of the Talus: Computer=assisted Retrograde Drilling Feasibility and Accuracy in Initial Experriences1", (Radiology. 2001;218:278-282) © RSNA, 2001.

Biomet/Copeland, "Aequalis® Resurfacing Head" Tomier, Scientific Vision, Surgical Leadership, SS-401 Jan. 2007.

Kumai, M.D., Tsukasa, et al Arthroscopic Drilling for the Treatment of Osteochondral Lesions of the Talus, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug.), 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Amette Blackwell SA.

Taranow WS, et al, "Retrograde drilling of osteochondral lesions of the medial talar dome", PubMed, www.pubmed.gov, A service of the National Library of Medicine and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan.), 2004: pp. 73-78.

Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Themen, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages).
APTA |Knee,/http://www.apta.org/AM/PrinerTemplate.cfm?Section=Home&TEMPLATE=CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php? pg=product_det_pm&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).
ART02.01 Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Office Action issued in corresponding U.S. Appl. No. 10/741,044 dated Oct. 26, 2005.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
United States Office Action issued is related U.S. Appl. No. 10/760,965 dated Feb. 19, 2008.
Australian Office Action issued in related Australian Patent Application No. 2003262428 dated Mar. 20, 2008.

Australian Office Action issued in related Australian Patent Application No. 2004293042 dated Feb. 20, 2008.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
U.S. Office Action issued in related U.S. Appl. No. 10/994,453 dated Sep. 3, 2008.
Canadian Office Action issued in related Canadian Patent Application No. 2546582 dated Aug. 21, 2008.
Supplemental Notice of Allowance dated Nov. 25, 2009 issued in related U.S. Appl. No. 10/373,463.
Office Action dated Dec. 24, 2009 issued in related U.S. Appl. No. 10/994,453.
Notice of Reasons for Rejection dated Nov. 17, 2009 issued in Japanese Patent Application No. 2007-519417.
European Search Report dated Dec. 3, 2009 issued in related European Patent Application No. 06735827.5.
U.S. Office Action dated Jan. 25, 2010 issued in related U.S. Appl. No. 11/326,133.
European Office Action dated Jan. 11, 2010 issued in related European Patent Application No. 2005218302.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Aug. 30, 2006 issued in related U.S. Appl. No. 10/618,887.
U.S. Office Action dated Jan. 15, 2008 issued in related U.S. Appl. No. 10/618,887.

U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Gelenkoberflachen, et al., "Partial hemi-resurfacing of the hip joint—a new approach to treat local osteochondral defects?" Biomed Tech 2006; 51:371-376 (2006).
Sullivan, "Hallux Rigidus: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Beecher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No, 2006501193.
Japanese Office Action dated Jan. 13, 2009 issued in Japanese Patent Application No, 2003552147.
International Search Report dated Jan. 30, 2006 issued in related International Patent Application No. PCT/US04/39181.
European Office Action dated Feb. 26, 2009 in related European Patent Application No, 05791453.3.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated Mar. 9, 2010 issued in related U.S. Appl. No. 11/359,892.
U.S. Office Action dated Feb. 2, 2010 issued in related U.S. Appl. No. 10/373,463.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Office Action dated Sep. 2, 2010 issued in related U.S. Appl. No. 12/415,503.
Office Action dated Aug. 30, 2010 issued in related U.S. Appl. No. 12/397,095.

Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
U.S. Office Action dated May 18, 2010 issued in related U.S. Appl. No. 12/415,503.
Australian Office Action dated Apr. 9, 2010 issued in related Australian Patent Application No. 2005260590.
European office communication dated Feb. 10, 2010 issued in European Patent Application No. 09002088.4-2310.
Australian Office Action dated Feb. 26, 2010 issued in related Australian Patent Application Mo. 200807536.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
International Preliminary Report on Patentability dated Sep. 16, 2010 issued in related International Patent Application No. PCT/US2009/035889.
Office Action dated Oct. 11, 2010 issued in related Australian Patent Application No. 2006216725.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
Notice of Allowance dated Jan. 5, 2011 issued in related U.S. Appl. No. 11/326,133.
Supplemental Notice of Allowance dated Jan. 5, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Sep. 9, 2010 issued in related U.S. Appl. No. 10/994,453.
Supplemental Notice of Allowance dated Oct. 6, 2010 issued in related U.S. Appl. No. 12/415,503.
Office Action dated Sep. 29, 2010 issued in related U.S. Appl. No. 11/461,240.
Supplemental Notice of Allowance dated Oct. 13, 2010 issued in related U.S. Appl. No. 10/994,453.
European Search Report dated Nov. 4, 2010 issued in related European Patent Application No. 07862736.1-1269.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12,582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated 11/23/11 issued in U.S. Appl. No. 11/623,513, 19 pages.
U.S. Office Action dated Nov. 28, 2011 issued in U.S. Appl. No. 12/711,039, 6 pages.
Examination Report dated Dec. 30, 2011 issued in European Patent Application No. 09 002 088.4, 6 pages.
Intent to Grant dated Feb. 17, 2012 isssued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Extended Search Report dated Jul. 3, 2012 issued in European Patent Application No. 12002103.5, 5 pages.

Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
Notice of Allowability dated Oct. 9, 2012, issued in U.S. Appl. No. 12/713,135, 5 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31, 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.

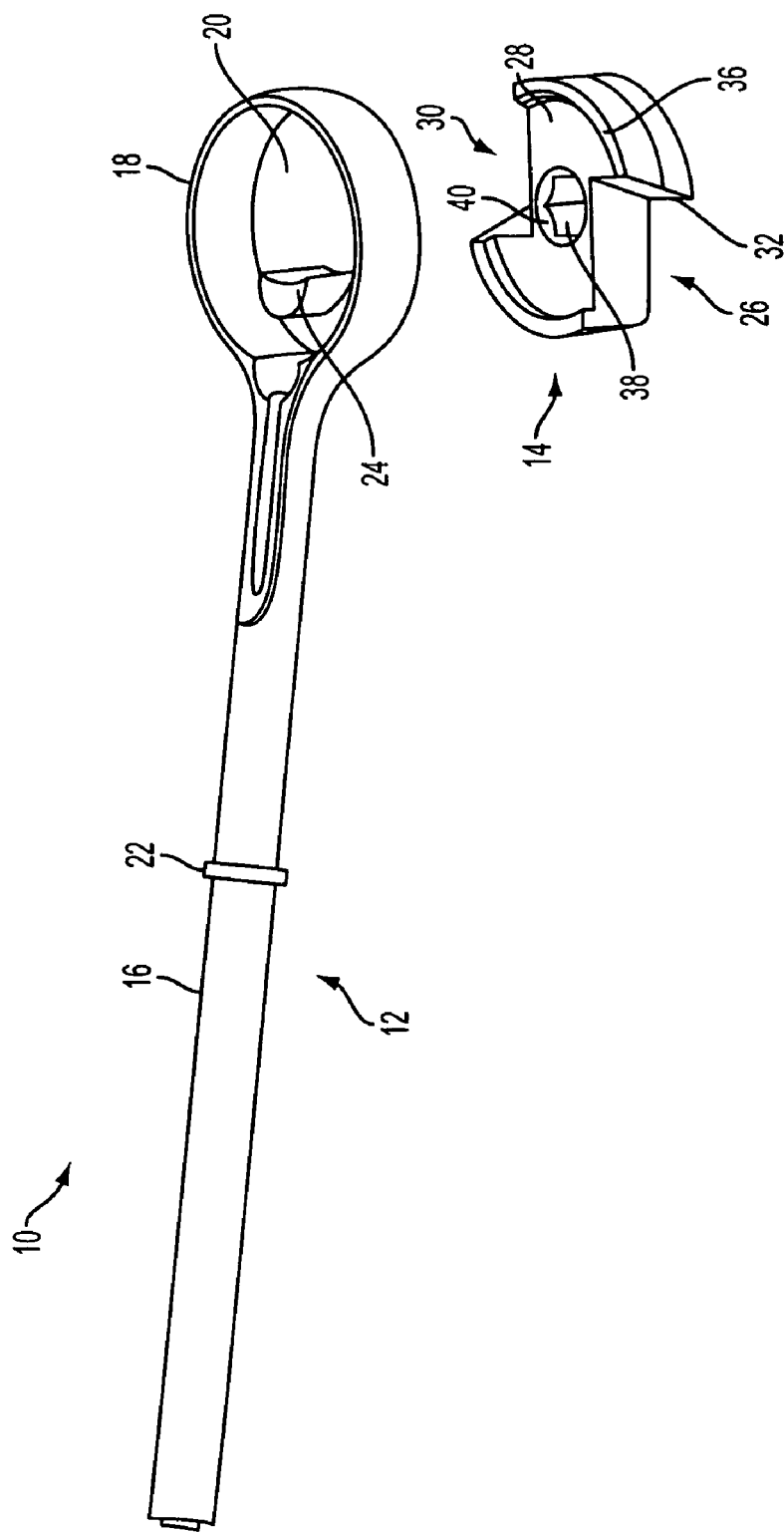

SYSTEM FOR ARTICULAR SURFACE REPLACEMENT

CROSS-REFERENCE TO RELATED APPLICATIONS

This application claims the benefit of U.S. provisional patent application Ser. No. 60/583,549, filed Jun. 28, 2004. This application is also a continuation-in-part of U.S. patent application Ser. No. 10/308,718, filed Dec. 3, 2002 now U.S. Pat. No. 7,163,541. This Application is also a continuation-in-part of U.S. patent application Ser. No. 10/994,453, filed Nov. 22, 2004, which claims the benefit of U.S. provisional patent application Ser. No. 60/523,810, filed Nov. 20, 2003, and which is a continuation-in-part of U.S. patent application Ser. No. 10/308,718, filed Dec. 3, 2002 now U.S. Pat. No. 7,163,541.

FIELD

The present disclosure relates generally to the replacement of a portion of an articular surface.

BACKGROUND

Articular cartilage, found at the ends of articulating bone in the body, is typically composed of hyaline cartilage, which has many unique properties that allow it to function effectively as a smooth and lubricious load-bearing surface. However, when injured, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

Hyaline cartilage problems, particularly in knee and hip joints, are generally caused by disease such as occurs with rheumatoid arthritis or wear and tear (osteoarthritis). Hyaline cartilage problems may also be the result of an injury, either acute (sudden) or recurrent and chronic (ongoing). Such cartilage disease or deterioration can compromise the articular surface causing pain and further deterioration of joint function. As a result, various methods have been developed to treat and repair damaged or destroyed articular cartilage.

For smaller defects, traditional options for this type of problem include non-operative therapies (e.g., oral medication or medication by injection into the joint), or performing a surgical procedure called abrasion arthroplasty or abrasion chondralplasty. The principle behind this procedure is to attempt to stimulate natural healing. At the defect site, the bone surface is abraded, removing approximately 1 mm. or less using a high-speed rotary burr or shaving device. This creates an exposed subchondral bone bed that will bleed and will initiate a fibrocartilage healing response. Although this procedure has been widely used over the past two decades and can provide good short term results, (1-3 years), the resulting fibrocartilage surface is seldom able to support long-term weight bearing, particularly in high-activity patients, and is prone to wear.

Another procedure, referred to as the "microfracture" technique, incorporates similar concepts of creating exposed subchondral bone. During the procedure, the cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique are generally similar to abrasion chondralplasty.

Another known option to treat damaged articular cartilage is a cartilage transplant, referred to as a Mosaicplasty or osteoarticular transfer system (OATS) technique. This technique involves using a series of dowel cutting instruments to harvest a plug of articular cartilage and subchondral bone from a donor site, which can then be implanted into a core made into the defect site. By repeating this process, transferring a series of plugs, and by placing them in close proximity to one another, in mosaic-like fashion, a new grafted hyaline cartilage surface can be established. The result is a hyaline-like surface interposed with a fibrocartilage healing response between each graft.

Such an OATS procedure is technically difficult, as all grafts must be taken with the axis of the harvesting coring drill being kept perpendicular to the articular surface at the point of harvest. Also, all graft placement sites must be drilled with the axis of a similar coring tool being kept perpendicular to the articular surface at the point of implantation. Further, all grafts must be placed so that the articular surface portion of these cartilage and bone plugs is delivered to the implantation site and seated at the same level as the surrounding articular surface. If these plugs are not properly placed in relation to the surrounding articular surface, the procedure can have a very detrimental effect on the mating articular surface. If the plugs are placed too far below the level of the surrounding articular surface, no benefit from the procedure will be gained. Further, based on the requirement of perpendicularity on all harvesting and placement sites, the procedure requires many access and approach angles that typically require an open field surgical procedure. Finally, this procedure requires a lengthy post-operative non-weight bearing course.

Transplantation of previously harvested hyaline cartilage cells from the same patient has been utilized in recent years. After the cartilage is removed or harvested, it is cultured in the lab to obtain an increase in the number of cells. These cells are later injected back into the focal defect site and retained by sewing a patch of periosteal tissue over the top of the defect to contain the cells while they heal and mature. The disadvantages of this procedure are its enormous expense, technical complexity, and the need for an open knee surgery. Further, this technique is still considered somewhat experimental and long-term results are unknown. Some early studies have concluded that this approach offers no significant improvement in outcomes over traditional abrasion and microfracture techniques.

BRIEF DESCRIPTION OF THE DRAWINGS

Features and advantages of the present invention are set forth by description of embodiments consistent with the present invention, which description should be considered in conjunction with the accompanying drawings wherein:

FIG. 1a is an exploded top perspective view of an embodiment of a low profile cutting system;

FIG. 3 depicts, in perspective view, one application of the cutting system shown in FIG. 1a;

FIG. 4 shows in side elevation one application of the cutting system illustrated in FIG. 1a;

DESCRIPTION

The present disclosure relates to a system for replacing a portion of an articular surface. While the methods and instruments described herein are particularly directed at the replacement of a portion of an articular surface of a femoral condyle and/or a tibial condyle, the system herein may suitable by employed for replacing a portion of other articular surfaces. Additionally, while the disclosure is relates to replacing a portion of each of two cooperating articular surfaces, the system herein may be used to replace only a portion of one articular surface of a joint, without necessitating the replacement of a cooperating articular surface of the joint.

Referring to FIGS. 1 through 9, a system for replacing a portion of an articular surface is disclosed. Generally, the disclosed system includes identifying a portion of an articular surface to be replaced, for example a damaged portion of the articular surface, or a portion including a lesion or defect, excising the identified portion of an articular surface to create an implant site and installing an implant in the implant site. The portion of the articular surface to be replaced herein may be identified arthroscopically, for example using either diagnostic or surgical arthroscopy. According to an embodiment, a portion of an articular surface of a tibia may be replaced. In such an embodiment, the knee joint may be partially opened by pulling the femur away from the tibia, to increase the clearance between the articular surface of the tibia being replaced and the cooperating articular surface of the femur. The increased clearance between the corresponding articular surfaces of the tibia and the femur may facilitate access to the identified portion of the articular surface of the tibia to enable excising the identified portion of the articular surface to create an implant site. According to another embodiment, at least a portion of the corresponding articular surface of the femur may be resected prior to replacing a portion of the articular surface of the tibia. Resection of at least a portion of the articular surface of the femur may provide an increase in the clearance between the articular surface of the tibia and the remaining corresponding portion of the femur. The resulting increased clearance may facilitate access to the articular surface of the tibia. An exemplary method for resecting at least a portion of the articular surface of the femur is discussed in detail infra.

Figure 1B:
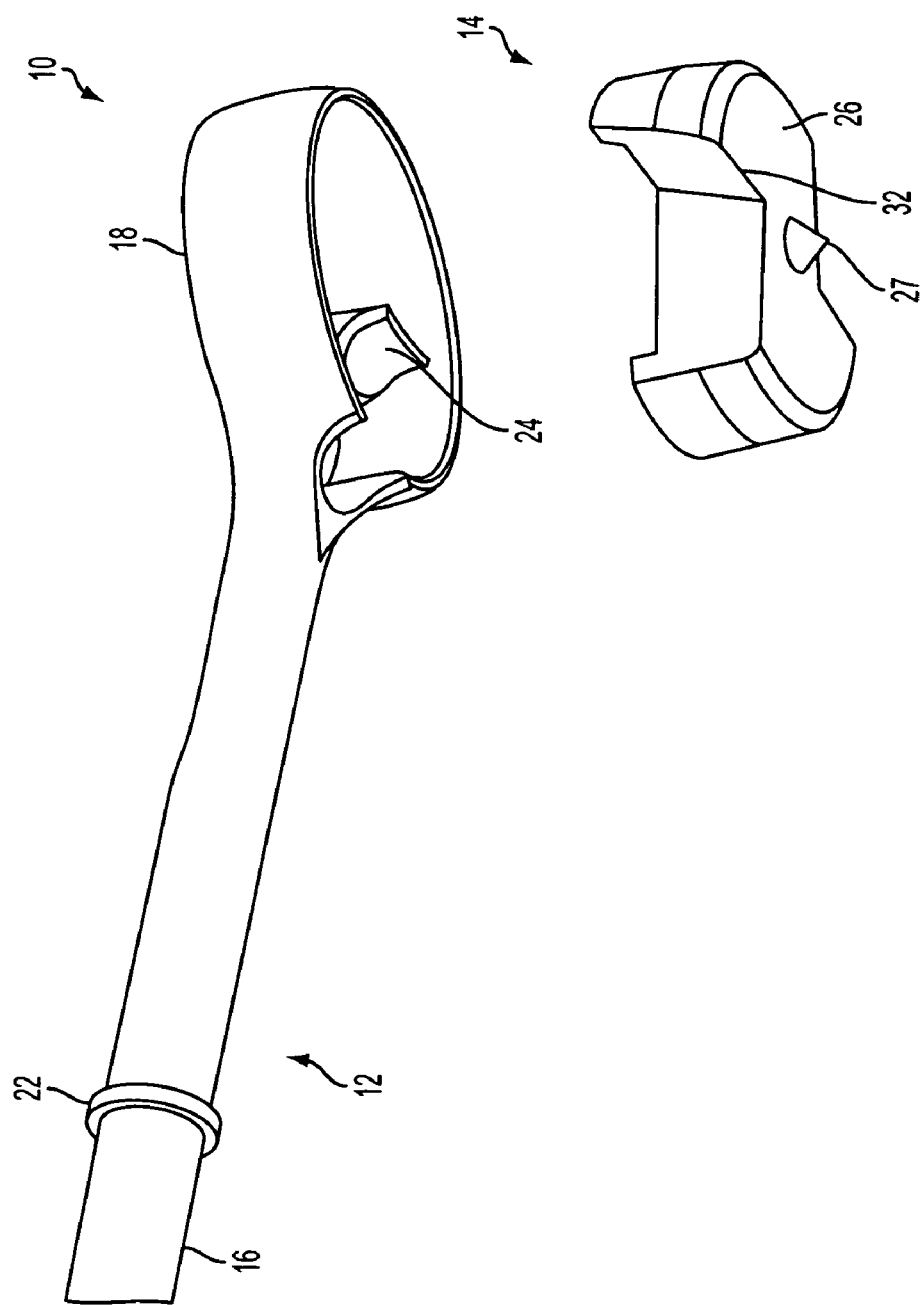
FIG. 1b is an exploded bottom perspective view of the cutting system shown in FIG. 1a, FIG. 2 is a perspective view of the low profile cutting system shown in FIG. 1a with the cutter assembled to the support member.
Figure 2:
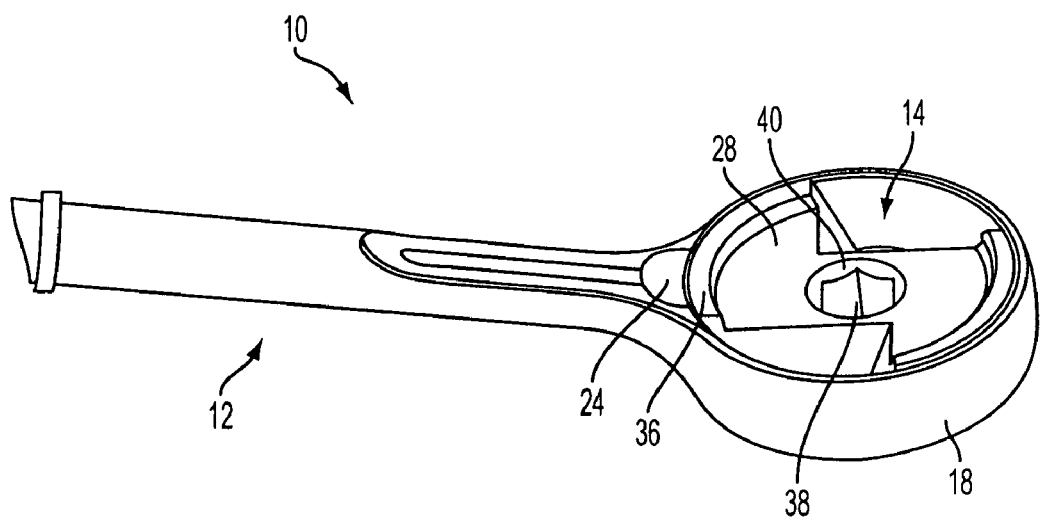

Turning first to FIGS. 1*a*, 1*b*, and 2, an embodiment of a low profile cutting system 10 is shown. The low profile cutting system 10 may generally include a support member, generally indicated at 12, and a cutter, generally indicated at 14. The support member 12 may include a shaft 16 including a cutter support 18 on the distal end thereof. The cutter support 18 may be provided as a ring or hoop and define a circular opening 20 sized to receive the cutter 14 therein, as shown in FIG. 2. The cutter support 18 may also be provided in configurations other than a ring or a hoop. For example, the cutter support 18 may have a square, rectangular, polygonal, oval, etc. shape in plan view, defining an opening for receiving the cutter 14.

The shaft 16 of the support member 12 may include a lumen, not shown, providing access via the shaft 16 to the opening 20 of the cutter support 18. The lumen defined by the shaft 16 may provide suction, supply a fluid, such as for flushing the region of the cutter support 18, etc. Alternatively, an inner shaft (not shown) may be translatably disposed at least partially within the lumen. The inner shaft may be at least partially extensible into the opening 20 defined in the support 18. The inner shaft may be urged into or towards the opening 20, for example, and act against an edge of a member disposed in the opening 20. The pressure of the inner shaft bearing against a member disposed in the opening 20 may aid in maintaining the member in the opening, for example, be creating a frictional interaction between the member and the support 18 and/or the inner shaft.

The shaft 16 may also include features, such as collar or ring 22, as well as other features and/or indicia along the length and/or circumference of the shaft 16 to facilitate manipulating the support member and/or for providing reference for use in conjunction with cooperating instruments. For example, the features or indicia may be used to align and/or position other instruments in a desired relationship with the support member and/or the cutter support 18 or opening defined therein.

The support member 12 may also include a shoe 24 that may be radially moveable into the opening 20. In one embodiment, the shoe 24 may form a portion of the circumference of the opening 20 in a retracted position, and extend into the opening 20 in a second position. The shoe 24 may be biased to a position extending into the opening 20, for example by a spring or a translatable shaft disposed in the lumen of the shaft 16. Accordingly, when the cutter 14 is disposed within the opening 20 the shoe 24 may be in a retracted position, i.e., at or withdrawn from the circumference of the opening 20, and when the cutter 14 is removed from the opening 20 the shoe 24 may be in an extended position, i.e., extending at least partially into the opening 20. In one embodiment, it is contemplated that the shoe 24 may have a height less that the height of the cutter support 18. Accordingly, the shoe 24 may move to an extended position when the cutter 14 is still partially received in the opening 20.

The cutter 14 may be formed having a generally circular cross-section sized to be rotatably received within the opening 20 of the support member 12. The diameter of the cutter 14 may be sized to allow the cutter 14 to be guided by the cutter support 18 with a minimal of play or run-out. The cutter 14 may be configured for cutting or boring in an axial direction.

The cutter 14 may include a cutting face 26. The cutting face 26 may engage an articular surface in which an implant site is to be formed. The cutting face 26 may include features suitable for excising the articular cartilage and/or underlying bone to form an implant site. According to one embodiment, cutting face 26 of the cutter 14 may include a taper, for example providing the cutting face 26 having a shallow conical surface. The cutting face 26 may also include a centering point 27. Consistent with the illustrated embodiment, the centering point 27 may be a conical protrusion, or other protrusion providing a point. The centering point 27 may establish, and maintain, the cutter 14 along an axis extending through the center of the cutter. Also as shown in the illustrated embodiment, the cutter 14 may include cut-outs, or flutes, 28, 30. The flutes 28, 30 may provide leading cutting edges, e.g. 32 in the illustrated embodiment, that are angled relative to the axis of the cutter 14. According to one embodiment, the flutes 28, 30 may have a helical configuration about the axis of the cutter 14. The illustrated embodiment of the cutter 14 includes two flutes 28, 30. However, alternative embodiments may be provided with a more or fewer flutes consistent with the present disclosure.

According to the above-described embodiment, the cutter 14 may be provided resembling a section of a twist drill bit. As such, when the illustrated cutter 14 is rotated in a clockwise direction the leading cutting edges 32 may cut into a surface or body to be excised, in a similar manner to a drill bit. The flutes 28, 30 may allow debris produces during excision to be evacuated from the implant site being formed, e.g. to the top of the cutter 14. Debris removed from the implant site being formed may be collected, for example using a suction device associated with, or positioned adjacent to the cutter support 18. Allowing debris to be evacuated from the implant site being formed may reduce compacting of debris at the sides of the cutter 14, binding of the cutter 14, and/or facilitate faster and more efficient excision of the articular surface and/or underlying bone.

According to another embodiment, the cutting face 26 of the cutter may include one or more cutting blades. The cutting blades may extend from the cutting face 26 either axially or at an angle to the axis of the cutter 14. Similarly, the cutting blades may be arranged extending radially or at an angle. According to various embodiments, the cutting blades may be integrally formed with the cutter, may be separate components fixed to the cutter, or may be replaceable components removably attached to the cutter. Similar to the illustrated embodiment, a cutter including cutting blades extending from the cutting face may include flutes to facilitate the removal of debris from an excision site.

The cutter 14 may also include a top face 34. The top face 34 may include an upstanding rib 36 around the circumference of the cutter 14. Effectively, the upstanding rib 36 may provide the top face 34 having a recessed configuration. The top face 34 may also be provided as a non-recessed feature, whereby the upstanding rib 36 may be eliminated.

Consistent with the present disclosure, the top face 34 may include a drive socket 38. The drive socket 38 may be configured to receive a cooperating drive element to allow the transmission of torque from the drive element to the cutter 14. As in the illustrate embodiment, the drive socket 38 may be configured as a hexagonal socket, which may receive a hexagonal end of a drive element to allow torque to be transmitted to the cutter 14 from the drive element. The socket 38 may include a chamfered upper edge 40 to facilitate insertion and engagement of a cooperating drive element. Various other socket configurations may suitably be employed to allow transmission of torque from a drive element to the cutter 14. For example, the socket 38 may include a splined socket, a flatted circular socket, a polygonal socket, etc. Additionally, it is contemplated herein that rather than a socket, the cutter may include a protrusion, such as a hexagonal protrusion, etc., that may be engaged by a socket on a drive element. Various other combinations of features may also suitably be used for transmitting torque between a drive element and the cutter.

Figure 3:
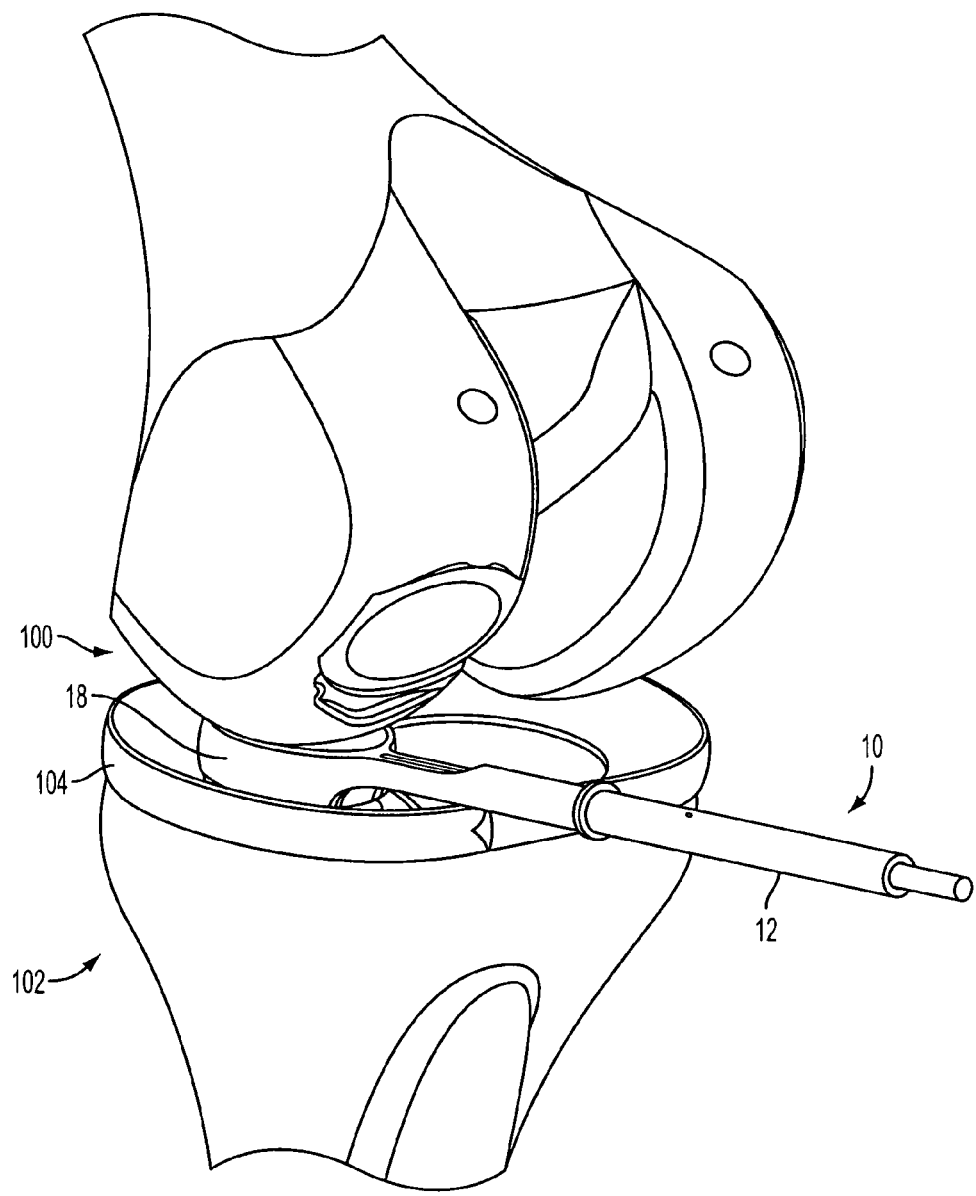
Figure 4:
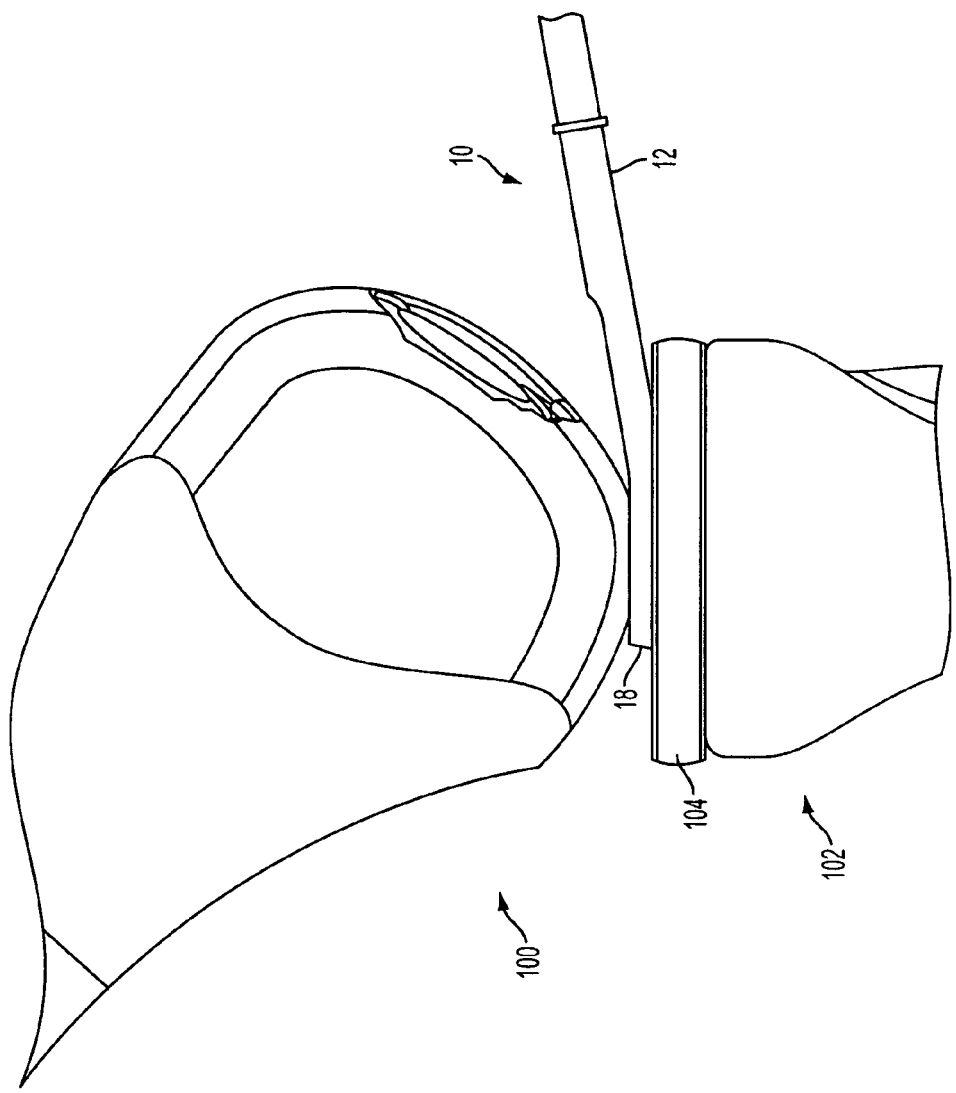

Turning to FIGS. 3 and 4, one application of a cutting system 10 according to the present disclosure is shown. Consistent with the illustrated application, the cutting system may be used to provide an implant site between two cooperating articular surfaces, for example between an articular surface of a femur 100 and an articular surface of a tibia 102. As shown, the shaft 12 may be manipulated to position the cutter support 18, including the cutter 14 received therein, within the joint between the cooperating articular surfaces of the femur 100 and tibia 102. According to one embodiment, the joint may be slightly opened by withdrawing the tibia 102 away from the femur 100 to at least slightly increase the clearance between the articular surfaces of the femur 100 and tibia 102.

Consistent with the system herein, at least a portion of the cooperating articular surface, e.g., an articular surface of the femur, may be resected prior to creating an implant site using the cutting system 10 herein. Resecting at least a portion of a cooperating articular surface may increase the clearance between the articular surfaces, thereby increasing access to the articular surface to be excised by the cutting system 10.

The shaft 16 may be manipulated to locate the opening 20 of the cutter support 18, and thereby locate the cutter 14, in a desired position on the articular surface. For example, the cutter 14 may be positioned generally centered over, or at least partially encompassing a defect in and articular surface. The defect may include, for example, a region of damaged articular cartilage, a lesion, etc. Furthermore, the cutter 14 may be positioned in a location of a desired auxiliary implant, such as an implant capable of interacting with an implant on a cooperating articular surface, for example to provide smoother operation or improved wear characteristics relative to native cartilage. Consistent with one embodiment, the shaft 12 may be manipulated to push the meniscus 104 aside with the cutter support 18. Accordingly it may be possible to directly expose an articular surface to the cutter 14. By employing such a technique, it may be possible to provide an implant on an articular surface of a knee without damaging the meniscus. By preserving the meniscus in this manner, it may be possible to provide a joint including articular surface implants having a smoother operation, better shock absorbing characteristics, better wear characteristics, and/or a more natural feel as compared to a joint including articular surface implants and having the meniscus removed. Preserving the meniscus is not, however, essential within the scope of the present disclosure.

Figure 5:
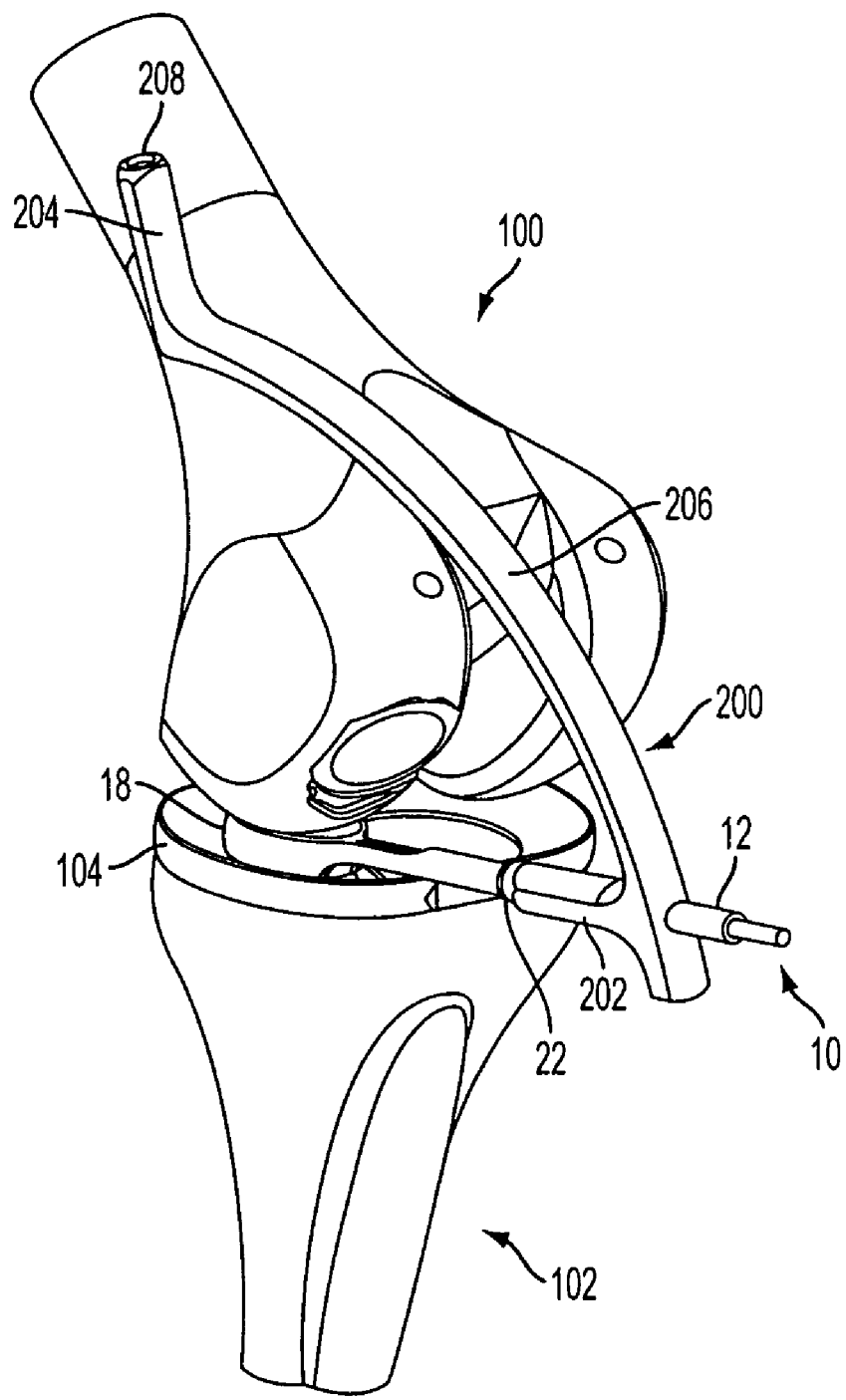
FIG. 5 illustrates an embodiment of a drill guide that may be used with a cutter system of the present disclosure.

Referring next to FIG. 5 a drill guide 200 that may be used in combination with the cutting system 10 is shown. The drill guide 200 may include a first alignment feature 202 that may be removably coupled to the cutting system 10 in a desired relationship. For example, the first alignment feature 202 may include a bore or opening capable of receiving the shaft 12 in a manner to align the first alignment feature 202 axially with the shaft 12. Consistent with one embodiment, the shaft 12 may be received through a bore in the first alignment feature 202 to permit the collar or ring 22 of the shaft 12 to bear against a portion of the first alignment feature 202, thereby locating the first alignment feature 202 along the axis of the shaft 12. The shaft 12 and/or the first alignment feature 202 may also include indicia and/or cooperating feature to achieve a desired radial alignment between the shaft 12 and the first alignment feature 202. Consistent with the present disclosure, the first alignment feature 202 and/or the shaft 12 may be capable of achieving a variety of desired relationships with respect to one another, e.g. by using sets of indicia or cooperating features. The first alignment feature 202 and/or the cutting system 10 may include a variety of elements, such as screws, snap-fits, etc. for removably coupling the first alignment feature 202 to the cutting system 10.

The drill guide 200 may also include a second alignment feature 204 coupled in a desired relationship to the first alignment feature 202 by a support structure 206. The support structure 206 may include an arm extending between the first and second alignment features 202, 204. In the illustrated embodiment the support structure 206 is provided as a continuous arcuate member. Various other embodiments of the support structure 206 may suitably be employed for providing a desired relationship between the first and second alignment features 202, 204. For example, the support structure 206 may include one or more straight sections and/or additional features.

Furthermore, consistent with one embodiment, the support structure 206 may be adjustable and/or capable of providing a plurality of relationships between the first and second alignment features 202, 204. The support structure 206 may be adjustably coupled to one or both of the first and second alignment features 202, 204. The support structure 206 may also, or alternatively, include adjustable portion along the extent of the support structure 206 capable of adjusting the relationship between the first and second alignment features 202, 204. One or more adjustable features of the drill guide 200 may include indicia and/or cooperating features to facilitate positioning the first and second alignment features 202 in desired and/or predetermined relationships relative to one another.

According to one embodiment the second alignment feature 204 may include a bore 208 extending therethrough. The drill guide 200 may be provided to position the bore 208 in predetermined relationship relative to the cutting system 10. According to one such embodiment the drill guide 200 may configured to provide a desired relationship between the bore 208 and the cutter 14 received in the cutter support 18 of the cutting system 10. For example, the drill guide 200 may be configured to align the bore 208 to have an axis that intersects the socket 38 of the cutter 14 at a desired angular relationship.

In one embodiment according to the present disclosure, the drill guide 200 may be coupled to the cutting system 10 to orient the bore 208 of the second alignment feature 204 along an axis that may intersect the socket 38 of the cutter 14. With the drill guide 200 provided in such an arrangement, a drill bit (not shown) may be disposed extending through the bore 208 of the second alignment feature 204. Using the drill bit, a hole may be drilled through a portion of the femur 100, including the articular surface thereof, to expose the socket 38 of the cutter 14.

Turning now to FIGS. 6 through 9, after a hole has been drilled to expose the socket 38 of the cutter 14, the cutting system 10 and drill guide 200 may be used to excise a portion of the articular surface of the tibia 102 and/or of the underlying bone. Once the hole, generally indicated at 300, has been drilled through the femur 100 extending to the articular surface thereof to expose the socket 38 of the cutter 14, the drill bit (not shown) may be withdrawn from the hole 300 and from the second alignment feature 204. A drive element 302 may then be inserted through the second guide feature 204 and through the hole 300 and engaged with the cutter 14.

Figure 7:
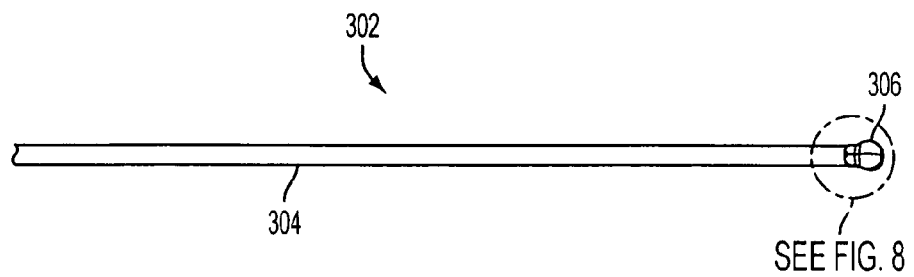
FIG. 7 depicts a drive element that may suitably be used for driving a cutter according to FIG. 1*a*.
Figure 8:
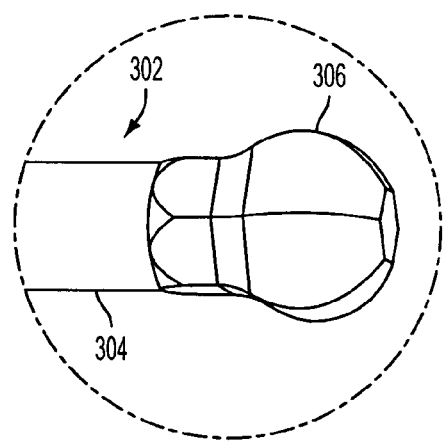
FIG. 8 is an enlarged view of the head of the drive element shown in FIG. 7.

Referring to FIGS. 7 and 8, an embodiment of a drive element 302 is shown. As depicted, the drive element 302 may include a shaft 304 portion and a head 306 portion. The shaft portion 304 may include a generally cylindrical shaft. A proximal end of the shaft 304 may be adapted to be engaged by a driver (not shown), such as a drill. While a cylindrical shaft may suitably be engaged by a conventional drill chuck, the proximal end of the shaft 304 may also include features specifically adapted for transmitting torque from the driver to the shaft 304. For example, the proximal end of the shaft may include flatted surfaces or the like to facilitating gripping of the shaft 304 as well as transmitting torque to the shaft 304. The proximal end of the shaft 304 may also include features capable of engaging with specific and/or proprietary drivers.

The head portion 306 of the drive element may include a feature capable of being received in and capable of engaging the socket 38 of the cutter 14. In the illustrated embodiment, the head 306 may include a feature having a hexagonal cross-section. The hexagonal cross-section of the head 306 may be sized to be received in the socket 38 and to transmit torque from the drive element 302 to the cutter 14. The head portion 306 may have different configurations, such as cross-sectional geometry, to suit different specific sockets 38. Furthermore, the head 306 of the drive element 302 may be provided including a socket in a case in which the cutter 14 is provided having a protrusion rather than a socket.

According to one embodiment, the head portion 306 may be configured as a ball-drive feature, as shown in the illustrated embodiment. The ball-drive head portion may allow the drive element 302 to transmit torque to the cutter in situations in which the drive element 302 is not coaxially aligned with the socket 38 and/or the cutter 14. As shown, a ball-drive head may include a generally rounded or spherical feature when viewed in profile. The rounded aspect of the ball-drive head portion 306 may allow the drive element 302 to pivot within the socket 38 generally about a center of the ball of the head portion 306. In such a manner, when torque is transmitted to the cutter 14 via the drive element, the ball-drive head portion 306 in combination the socket 38 may perform in a manner similar to a universal, or flex, joint between the cutter 14 and the shaft portion 304 of the drive element 302. Accordingly, utilizing a ball-drive head portion 306, while not necessary, may increase the acceptable tolerance relative to the alignment of the drive element 302 and the socket 38 and/or cutter 14.

In the illustrated embodiment, the ball-drive head portion 306 is shown having a diameter that is larger than the diameter of the shaft portion 304. This configuration may allow the drive element 302 to transmit torque to the cutter 14 even when the drive element 302 is out of alignment with the axis of the cutter 14. In some cases the drive element 302 may be able to transmit torque to the cutter 14 up to an angle at which the shaft portion 302 begins to bind or drag against an upper edge of the socket 38, e.g., the chamfered upper edge 40.

In another embodiment, the shaft portion 304 of the drive element may have a diameter that is equal to, or greater than, the head portion 306 of the drive element 302. According to such an embodiment, it may still be possible to provide the drive element 302 including a ball-drive head portion 306, thereby allowing a margin or misalignment between the drive element 302 and the cutter 14. When the shaft portion 304 is provided having a diameter equal to or greater than the head portion 306, the head portion 306 may be provided having a ball-drive configuration by providing a neck disposed between the shaft portion 304 and the head portion 306. The neck may include a region having a smaller diameter than the shaft portion 304 or the head portion 306. The neck may include a transition region extending between the region having a smaller diameter and each of the shaft portion 304 and the head portion 306. The neck may allow some misalignment between the drive element 302 and the cutter 14 by allowing the ball-drive head portion 306 to rotate in the socket 38 without the shaft portion 304 of the drive element 302 binding against and edge of the socket 38.

Figure 6:
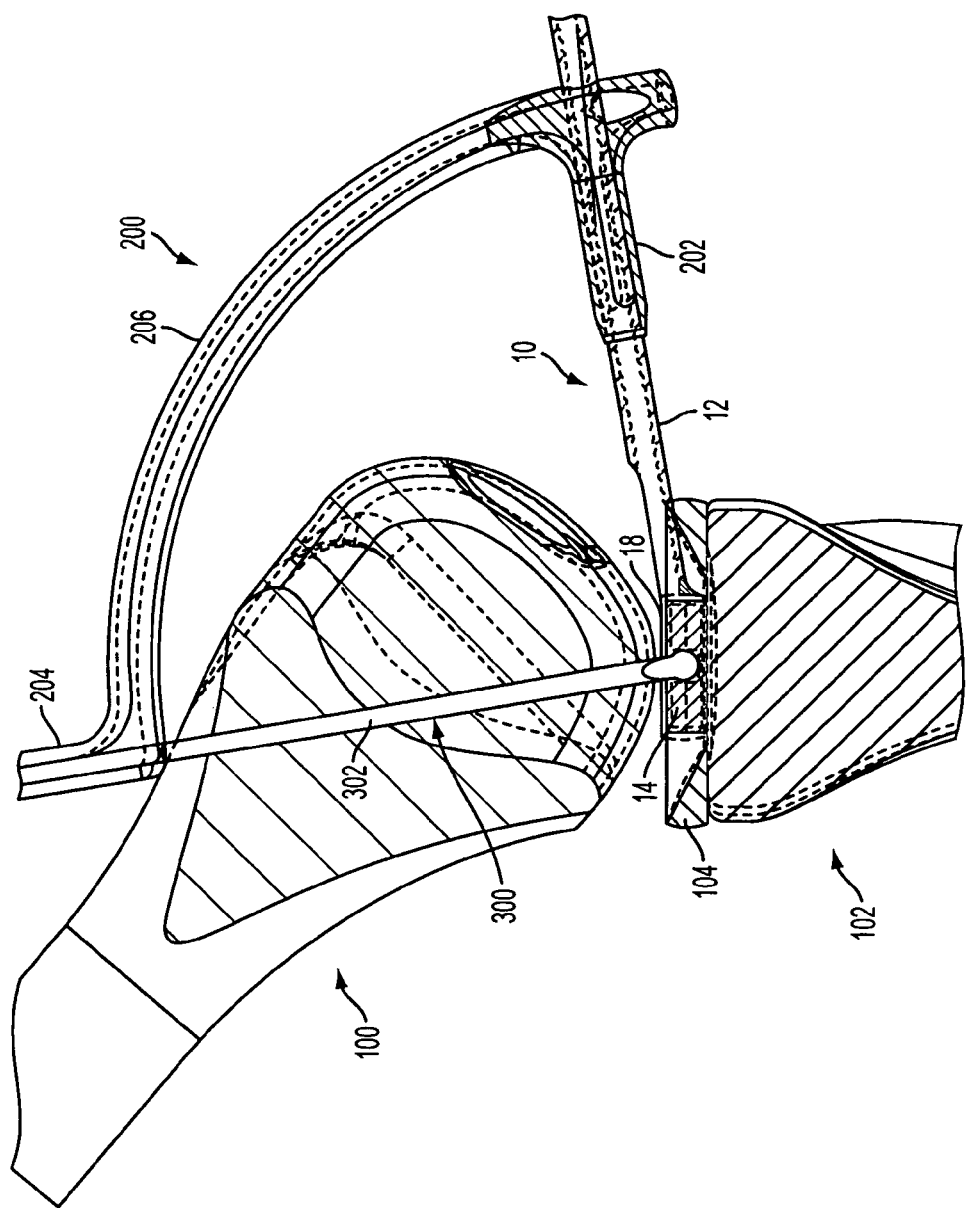
FIG. 6 is a cross-sectional view schematically illustrating the use of a cutting system and drill guide according to the present disclosure to excise an articular surface.
Figure 9:
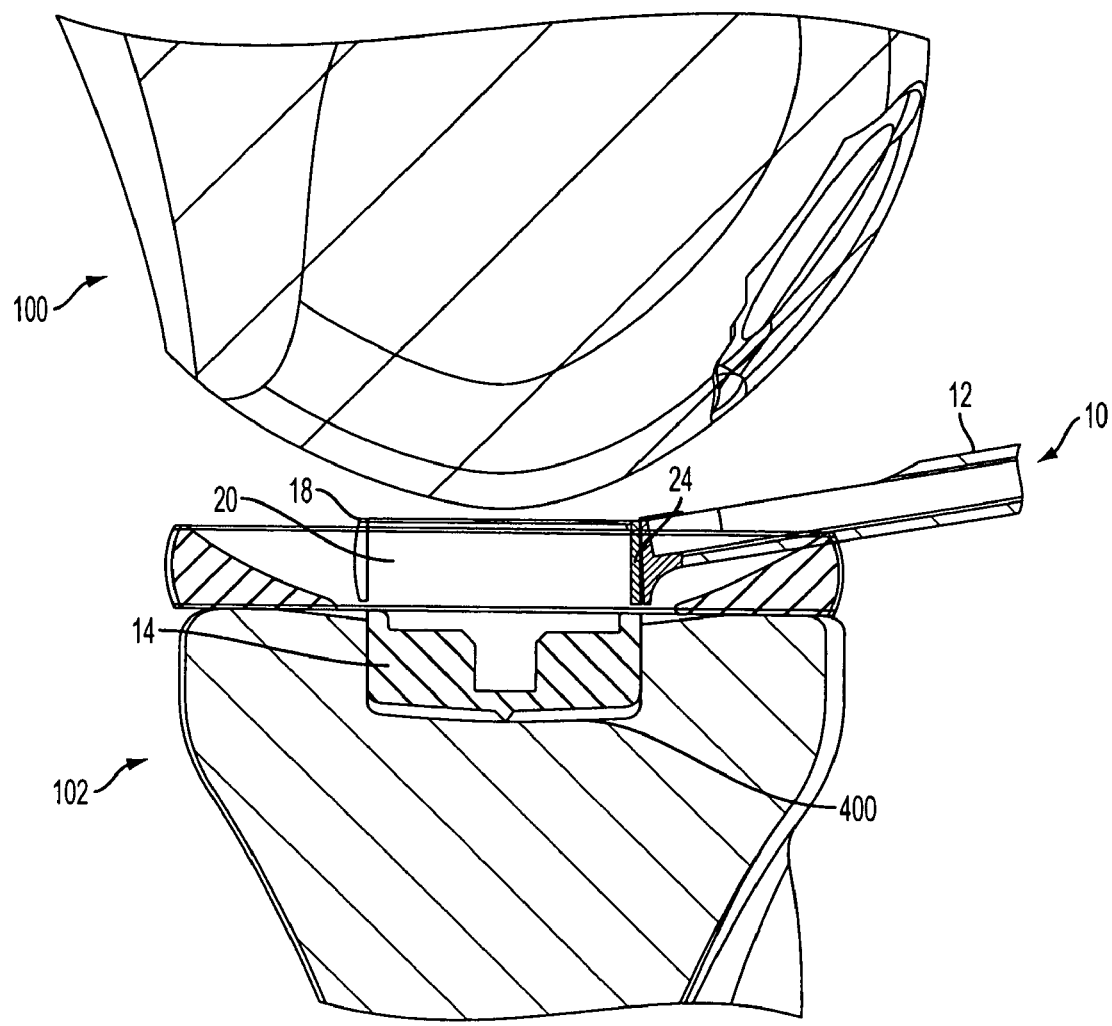
FIG. 9 is a cross-sectional view shown an articular surface including a region excised using a cutting system according to the present disclosure.

As shown in FIG. 9, the overall system illustrated in FIG. 6 may be used to excise a portion of an articular surface, of a tibia in the case of the illustrated embodiment, as well as a portion of the bone underlying the articular cartilage, to provide an implant site 400. The implant site 400 may be formed by driving the cutter 14 with a driver, such as a power drill, via the drive element 302. The cutter 14 may be driven until the implant site 400 has been excised to a desired depth. According to one embodiment, the depth of the implant site may be gauged using the shoe 24. The shoe 24 may be biased toward a position extending into the opening 20 of the cutter support 18. As the cutter 14 is driven to a depth below a bottom edge of the shoe 24 the shoe 24 may move into a position extending into the opening 20 as a result of the spring bias. The movement of the shoe 24 into an extended position may be visually perceptible, or may trigger an alert condition. The alert condition may include an audible or visual indicator that may result from an electrical signal generated by the movement of the shoe 24 into the extended position, or may be caused by a mechanical actuation as a result of the movement of the shoe 24 into the extended position. Other methods and apparatus for determining the depth of an excised implant site 400 may also be employed consistent with the present disclosure.

After an implant site 400 having a desired depth has been excised, the cutter 14 may be extracted. In an embodiment the cutter 14 may be extracted by withdrawing the cutter 14 back into the opening 20 of the cutter support 18. The cutter 14 may then be withdrawn from the joint site by extracting the cutting system 10, including the cutter 14, cutter support 18, and shaft 12, as a single unit. The cutter 14 may be withdrawn back into the opening 20 of the cutter support 18 using, for example, a pick that may be manipulated extending through the hole 300 previously created extending through at least a portion of the femur. The pick may pull the cutter 14 upwardly from the implant site 400 and into the cutter support. According to one embodiment, the drive element 302 may be employed to withdrawn the cutter 14 into the cutter support 18. In such an embodiment, the drive element 302 may be provided with a means for releasably retaining the cutter 14. The drive element 302 may include, for example, an extendable feature from the head portion 306 capable of releasably retaining the cutter 14. In an embodiment of the cutting system 10 including a biased shoe 24, the shoe 24 may first be withdrawn into a retracted position before the cutter 14 is withdrawn into the cutter support 18.

According to another embodiment, the cutter support 18 may first be withdrawn from the joint site. The cutter 14 may then be extracted from the implant site 400. In one such embodiment, the cutter 14 may be extracted using, for example, a pick or other retraction device operating between the articular surfaces of the femur 100 and tibia 102. Additionally, or alternatively, a retraction device operating through the hole 300 previously created extending through at least a portion of the femur may be used to extract the cutter 14 from the implant site 400, and from the joint site.

Figure 10:
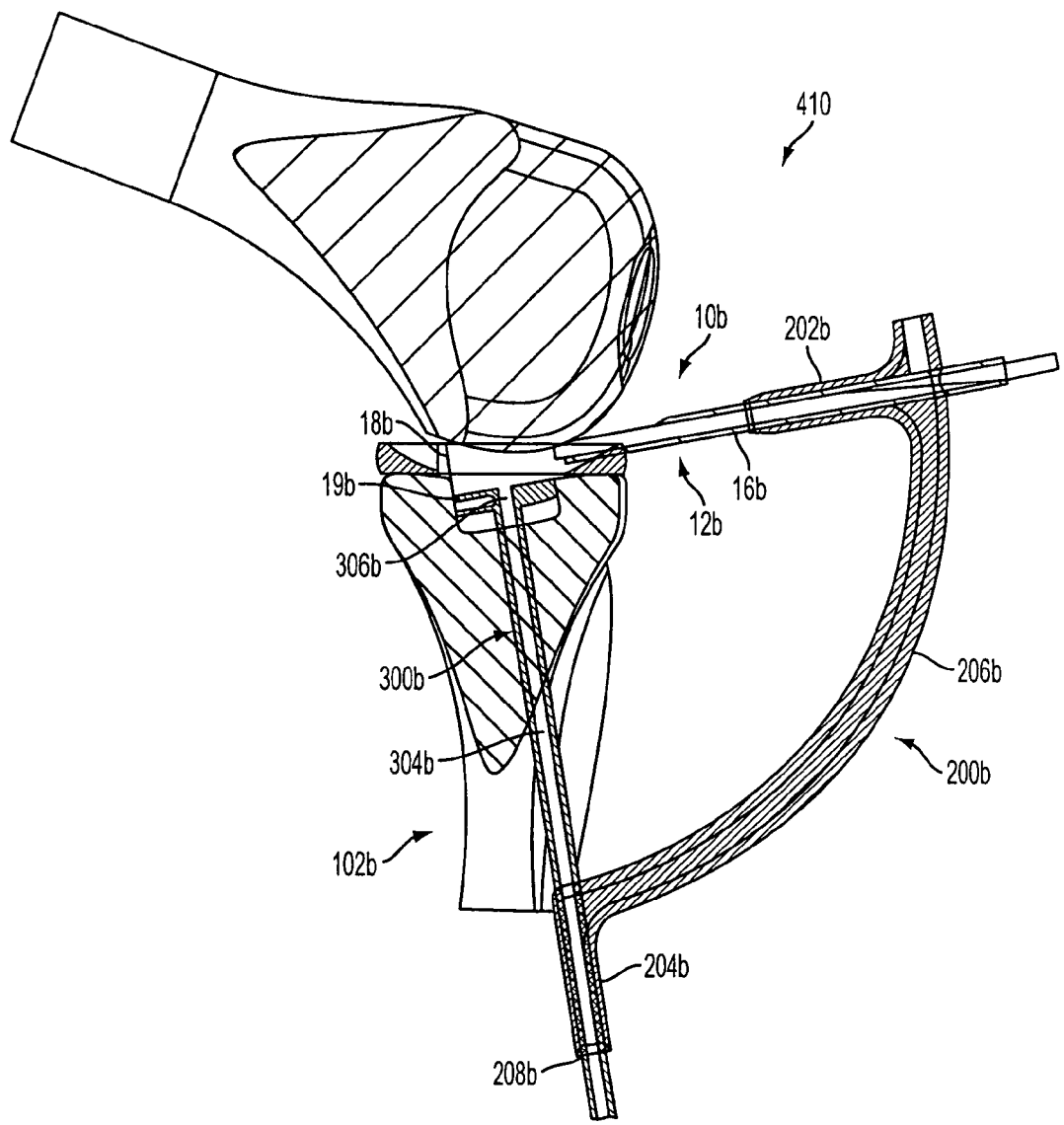
FIG. 10 is a cross-sectional view schematically illustrating another embodiment of a cutting system and drill guide according to the present disclosure.
Figure 11:
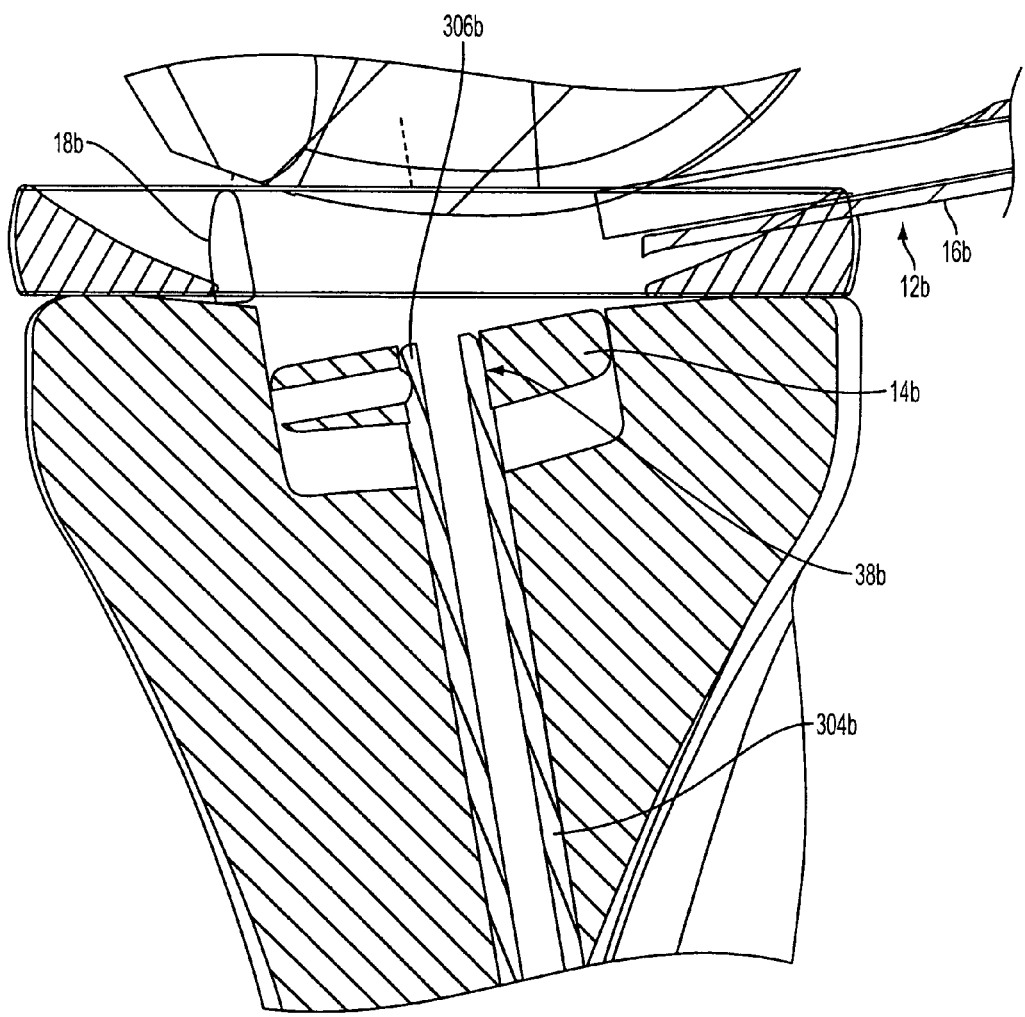
FIG. 11 is an enlarged view of the cutting system and drill guide of FIG. 10 being used to excise a region of an articular surface.

Referring to FIGS. 10 and 11, another embodiment of a system 410 that may be employed to excise at least a portion of an articular surface is shown. As with the previous embodiment, the system 410 may generally include a cutting system 10b and a drill guide 200b. The cutting system 10b may generally include a support member 12b and a cutter 14b. The support member may include a shaft 16b extending from a cutter support 18b that includes an opening for receiving a cutter 14b. The system 410 may also include a drill guide 200b that may be used in combination with the cutting system 10b to excise a portion of an articular surface of a joint. The drill guide 200b may generally include a first alignment feature that may be removably coupled to the shaft 16b of the cutting system 10b in a desired angular and/or rotational relationship. For example, in the illustrated embodiment, the first alignment feature 202b includes a bore adapted to receive the shaft 16b of the cutting system 10b. The bore and/or the shaft 16b may include cooperating features and/or indicia to facilitate achieving a desired alignment. Such cooperating features and/or indicia may allow variable desired alignments to be achieved.

The drill guide 200b may also include a second alignment feature 204b coupled in a desired relationship to the first alignment feature 202b by a support structure 206b extending between the first alignment feature 202b and the second alignment feature 204b. As in the illustrated embodiment, the support structure 206b may be configured as a continuous arc formed from a single piece. According to alternative embodiments, the support structure 206 may include adjustment features that enable the relationship between the first alignment feature 202b and the second alignment feature 204b to be varied. The adjustment features may include indicia or cooperating features that enable the first alignment feature 202b and second alignment feature 204b to be positioned in a desired predetermined relationship to one another. Furthermore, the support structure 206b may be formed from generally straight components and/or components having both straight and arcuate regions.

Similar to the previous embodiment, the second alignment feature 204b may include a bore extending through the second alignment feature 204b. The bore 208b may be adapted to receive a drill bit (not shown) or similar tool therethrough. The bore 208b of the alignment feature may be provided to position the drill bit in a desired orientation relative to the cutting system 10b. According to one embodiment, the drill guide 200b may be configured to position a drill bit to intersect the cutter support 18b in a central region and aligned generally normal to the cutter 14b. As with the previous embodiments, the bore 208b of the second alignment feature 204b may also be adapted to rotatably receive a drive element therethrough. In use, the drill guide 200b may be coupled to the cutter system 10b such that the second alignment feature 204*b* may be positioned to intersect a central region of the cutter support 18*b* along an axis that is generally normal to the cutter 14*b*.

With further reference to the enlarged view of FIG. 11, the cutter 14*b* may include a generally centrally located opening 38*b* extending into the cutter 14*b* from the bottom thereof. The opening may define a socket 38*b*, and as such may be have a splined, keyed, polygonal, etc. configuration allowing torque to be transmitted to the cutter 14*b*. According to one embodiment, the socket 38*b* may extend all of the way through the cutter 14*b*. As shown in FIGS. 10 and 11, the cutting system 10*b* may be positioned within the joint so that the cutter support 18*b*, and the cutter 14*b* disposed therein, is generally centered about a desired excision site. The drill guide 200*b* may be coupled to the cutting system 10*b* and oriented so that the second alignment feature 204*b* is generally aligned along an axis that intersects the center of the cutter 14*b* and is generally oriented normal to the cutter 14*b*. A drill bit may be positioned extending through the second alignment feature 204*b*, and a hole 300*b* may be drilled through the tibia 102*b*, in the illustrated embodiment. The hole 300*b* may be drilled extending through the tibia 102*b* up to an articular surface thereof. The hole 300*b* may extend through the articular surface of the tibia 102*b* and provide access to the socket 38*b* in the bottom side of the cutter 14*b* facing the articular surface of the tibia 102*b*.

With the hole 300*b* providing access through the tibia 102*b* to the socket 38*b* of the cutter 14*b*, a drive element including a drive shaft 304*b* and a drive head 306*b* may be inserted through the second alignment feature 204*b* of the drill guide 200 and through the hole 300*b* in the tibia 102*b*. A proximal end of the drive shaft 304*b* may be adapted to be engaged by a driver (not shown), such as a drill. The drive head 306*b* may be adapted to be received in the socket 38*b* of the cutter 14*b*. The drive head 306*b* may also be adapted for transmitting torque through from the drive shaft 304*b* to the cutter 14*b*. For example, the drive head 306*b* and socket 38*b* may each have a polygonal profile, such as a hexagonal profile. Alternatively, the ball drive 306*b* and the socket 38*b* may include features such as flats, splines, keys, etc. to facilitate the transmission of torque from drive shaft 304*b* to the cutter 14*b*.

In addition to the torque transmitting features of the drive head 306*b* and the socket 38*b*, the drive head 306*b* and the socket 38*b* may include cooperating locking features. The locking features herein may operate to selectively prevent axial extraction of the drive head 306*b* from the socket 38*b*. Consistent with the illustrated embodiment, the locking feature may include an indentation 308 in the drive head 306*b*. The indentation 308 may be configured as a recess or opening in the outer circumference of the drive head 306*b*. According to alternative embodiments, the indentation 308 may include, for example, a groove around the exterior of the drive head 306*b*. The cutter 14*b* may include a cooperating detent (not shown) for engaging the indentation in the drive head 306*b*. According to an embodiment herein, the cutter 14*b* may include a radial opening 42. The opening 42 may house a plug (not shown) such as a cylindrical member, a ball, etc. that may be biased, e.g., by a spring, toward the interior of the socket 38*b*. Consistent with such an arrangement, when the drive head 306*b* is inserted into the socket 38*b* the plug may be radially displaced toward the circumference of the cutter 14*b*. Once the drive head 306*b* has been inserted into the socked 38*b* such that the indentation 308 is generally aligned with the opening 42, the biased plug may move toward the center of the cutter 14*b* and a portion of the plug may engage the indentation 308 in the drive head 306*b*. According to such an embodiment, the drive head 306*b* may be releasably engaged with the cutter 14*b* and resist axial extraction of the drive head 306 from the socket 38*b* until an extracting force is applied to the drive head 306*b* sufficient to overcome the bias on the plug and force the plug toward the circumference of the cutter 14*b*. Various other locking features and mechanism may also be employed for releasably engaging the drive head 306*b* in the socket 38*b*.

The drive shaft 304*b* and/or the drive head 306*b* may also include features that permit engagement between the drive head 306*b* and the socket 38*b* even in the event of a slight to moderate misalignment between drive shaft 304*b* and the cutter 14*b*. As in previous embodiments, the drive head 306*b* may include a ball drive configuration. As discussed above, a drive ball configuration of the drive head 306*b* may allow the connection between the drive head 306*b* and the socket 38*b* to operate in a manner similar to a universal joint. Similarly, the drive shaft 304*b* may include a flexible section, for example, disposed adjacent the drive head 306*b*. Other similar features may also be employed.

Consistent with the foregoing, once the drive head 306*b* is received in the socket 38*b* and axially locked in the socket 38, an implant site may be excised in an articular surface of the tibia 102*b* using the cutter 14*b*. A driver, for example a power drill, may be used to rotationally drive the cutter 14*b* via the drive shaft 304*b* and drive head 306*b* engaged in the socket 38*b*. As the cutter 14*b* is being rotationally driven by the driver, an axially withdrawing force may be applied to the drive shaft 304*b* urging the cutter 14*b* into the articular surface being excised, e.g. an articular surface of a tibia in the illustrated embodiment. The locking feature coupling the drive head 306*b* to the socket 38*b* may prevent the drive head 306*b* from being extracted from the socket 38*b*, and therefore allow the axially withdrawing force applied to the drive shaft 304*b* to be transmitted to the cutter 14*b*, and thereby urge the cutter into the articular surface. From a general standpoint, the cutter 14*b* is being rotated and pulled into the articular surface.

The cutter 14*b* may be driven until the articular surface has been excised to a desired depth. The depth of the excised site may be monitored and/or checked using a variety of techniques. On such technique is simple observation at the articular surface, e.g., viewing through the cutter support 18*b*. A biased shoe may also be used to monitor the depth of the excision. That is, the cutting system 10*b* may include a shoe biased toward a position extending inwardly into the cutter support 18*b*, wherein movement of the shoe to an extended position may be impeded by the cutter 14*b*. When the excision depth is sufficient that the cutter 14*b* is below the shoe, the shoe may move inwardly to an extended position. The movement and/or the position of the show may be visibly perceptible, and/or may be coupled to an indication system providing visible and/or audible indication that the shoe has moved to an extended position. According to still another embodiment, the drive shaft 304*b* and/or the second alignment feature 204*b* may include indicia representative of the position of the cutter 14*b* when the drive head 306*b* is received in the socket 38*b* of the cutter 14*b*. As the articular surface is excised and the cutter moves into the articular surface the drive shaft 304*b* may be extracted from the second alignment feature 204*b* a corresponding distance. The depth of the excised site may, therefore, be determined by reference to the amount the drive shaft 304*b* is withdrawn.

Figure 22:
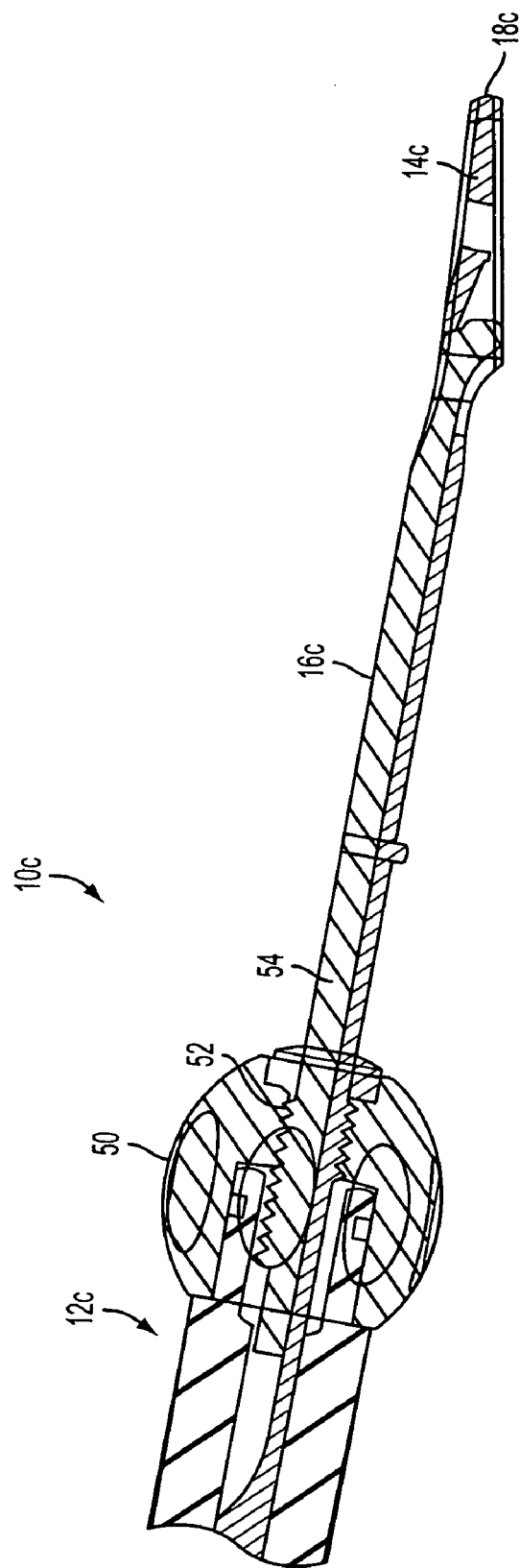
FIG. 22 is an enlarged cross-sectional view of the cutting system illustrated in FIG. 21.
Figure 23:
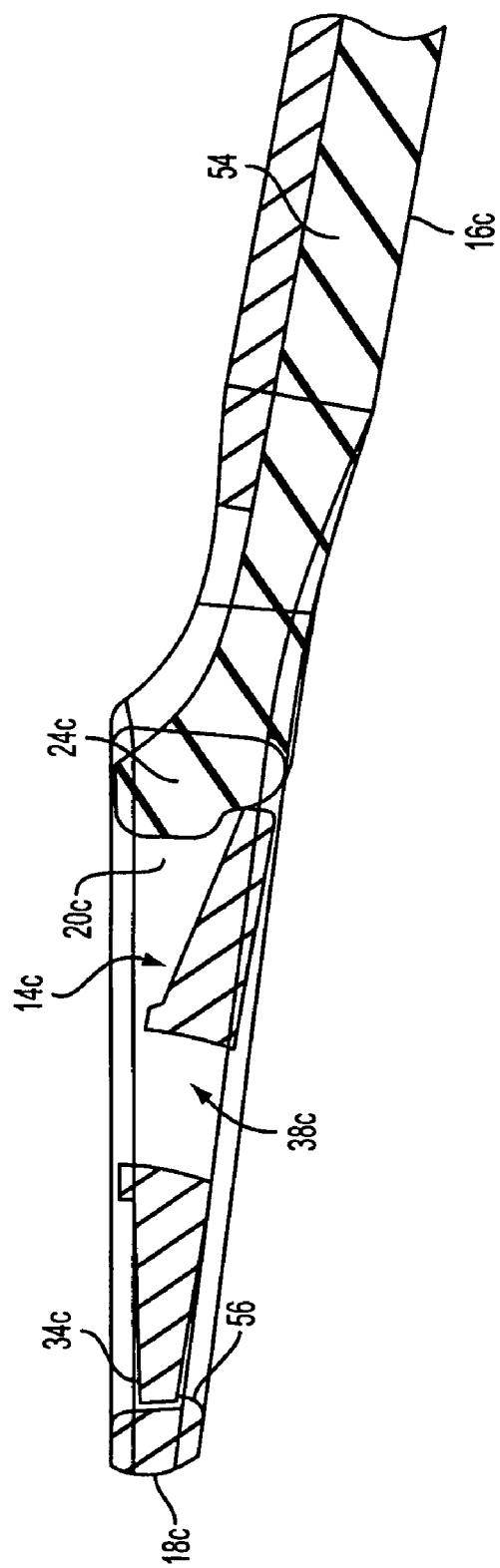
FIG. 23 is an enlarged cross-sectional view of the cutter support of the cutting system illustrated in FIG. 21.

Referring to FIGS. 21 through 24, an embodiment of a cutting system 10*c* may be provided in which the cutter support 18*c* may be provided having a low profile, that is, the height of the cutter support 18*c* along the axis of the opening 20*c* may be small enough to allow the cutter support 18*c* to be inserted in between the cooperating articular surfaces of the femur 100 and tibia 102. According to the illustrated embodiment, the cutter support 18c may be distally tapered such that the proximal end of the cutter support 18c has a greater height than the distal end of the cutter support 18c. As best seen in FIG. 23, the cutter 14c may also be provided having a low profile to be received in the low profile cutter support 18c. As such, the top surface 34c of the cutter 14c may be radially tapered such that the center of the cutter 14c in the region of the socket 38c may have a height that is greater than the height of the cutter 14c at the outer edge thereof.

With reference to FIGS. 22 and 23, the cutting system 10c may include an internally threaded knob 50 rotatably disposed on the support member 12c. The internal threads 52 of the knob 50 may engage a threaded portion of a translatable shaft 54 disposed within a lumen of the shaft 16c. Rotation of the knob 50 may act to advance or withdraw the shaft 54 relative to the cutter support 18c. The translatable shaft 54 may be either directly or indirectly coupled to the shoe 24c. Advancing the translatable shaft 54 may cause the shoe 24c to bear against the circumference of the cutter 14c. According to one embodiment, when the shoe 24c may bear against the circumference of the cutter 14c, the cutter may translate slightly and engage a lip 56 on the cutter support 18c, thereby securely retaining the cutter 14c in the cutter support 18c. The cutter 14c may be released by rotating the knob 50 to withdraw the shoe 24 from the circumference of the cutter 14c.

Figure 24:
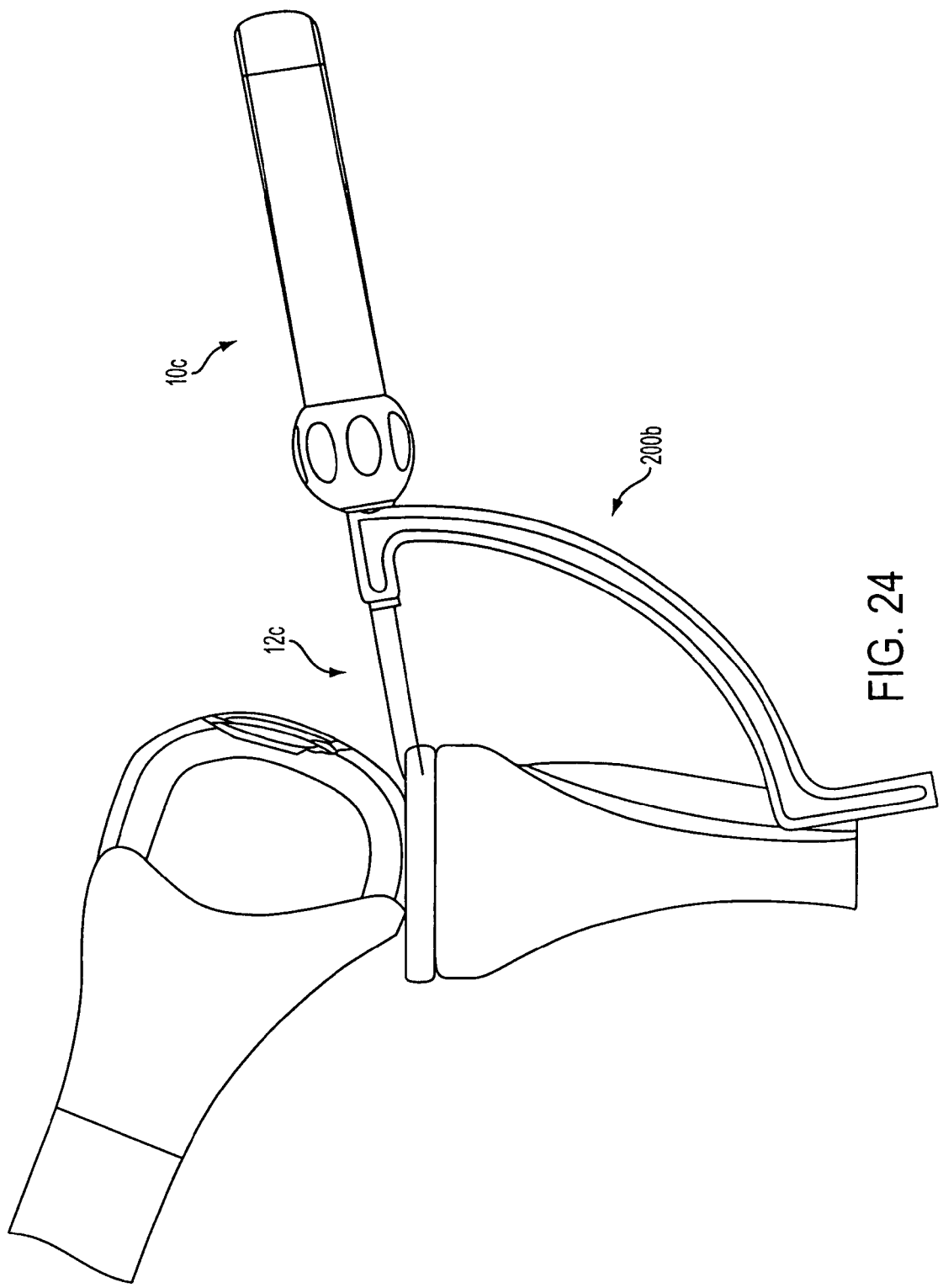
FIG. 24 illustrates the cutting system show in FIG. 21 being employed in conjunction with a drill guide.

As shown in FIG. 24, the low profile cutting system 10c may be used in a manner similar to the previously described cutting systems. For example, the cutting system 10c may be used in conjunction with a drill guide 200b and a cutter drive (not shown) to excise an implant site consistent with the previously described methodologies. While the illustrated drill guide 200b is adapted for accessing and driving the cutter 14c through the tibia, the low profile cutting system may also be used in conjunction with other drill guides and drive systems, including the drill guide 200 illustrated in FIGS. 5 and 6, as well as drill guides and drive systems having various other configurations.

While the foregoing description of the embodiments of cutting systems, drill guides, and associated methods have been described with reference to excising a portion of an articular surface of a tibial condyle, the disclosed systems and methods may suitable be applied to various other articular surfaces. The specific embodiments should, therefore only be construed as illustrative but not as limiting.

Figure 12:
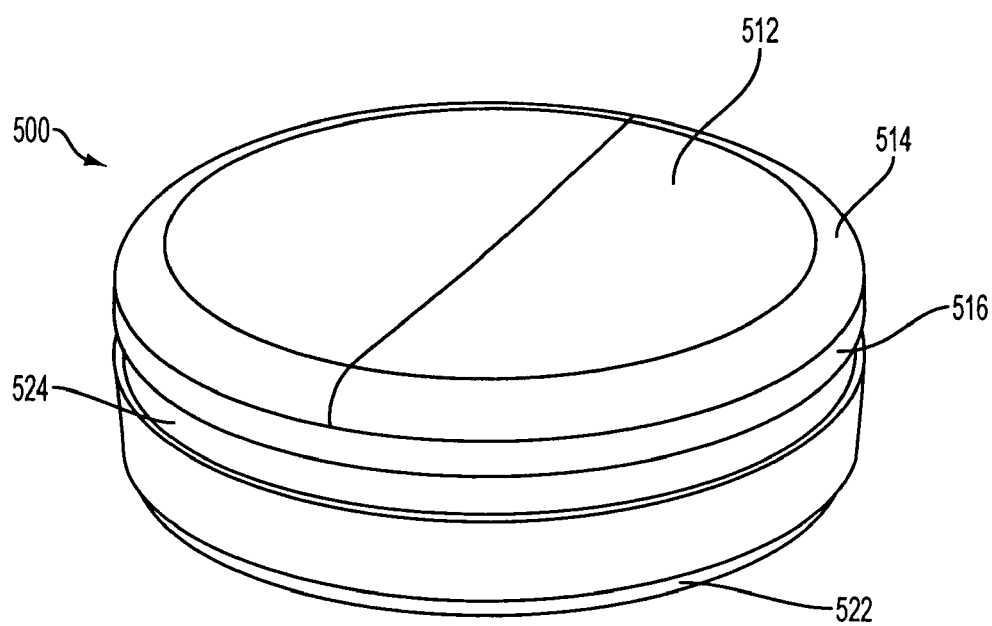
FIG. 12 is a top perspective view of an embodiment of a first implant.
Figure 13:
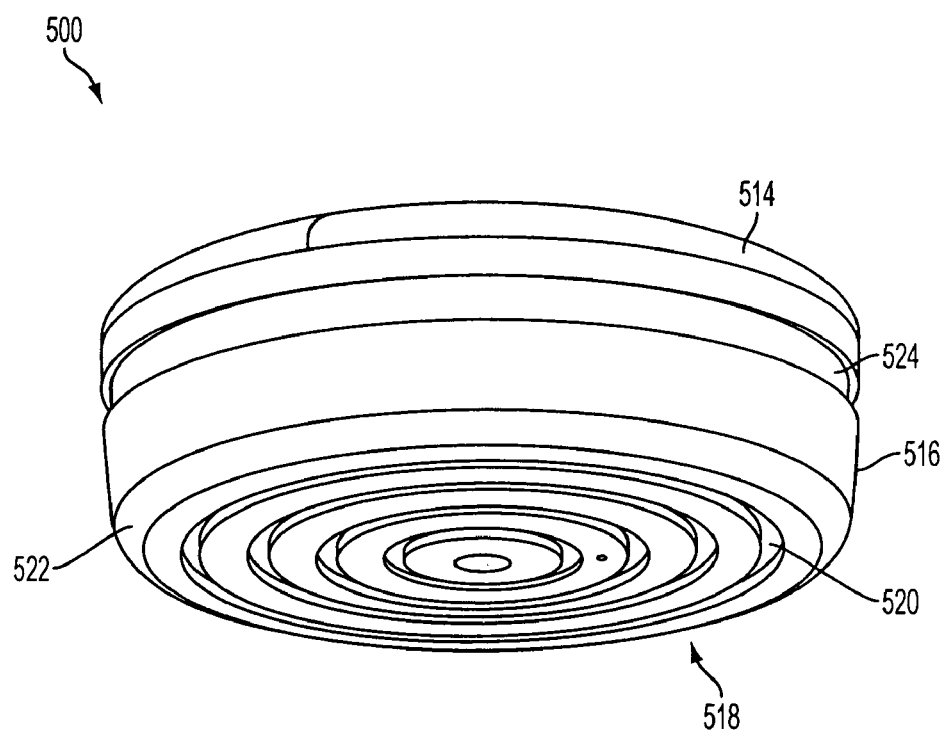
FIG. 13 is a bottom perspective view of the first implant shown in FIG. 12.
Figure 14:
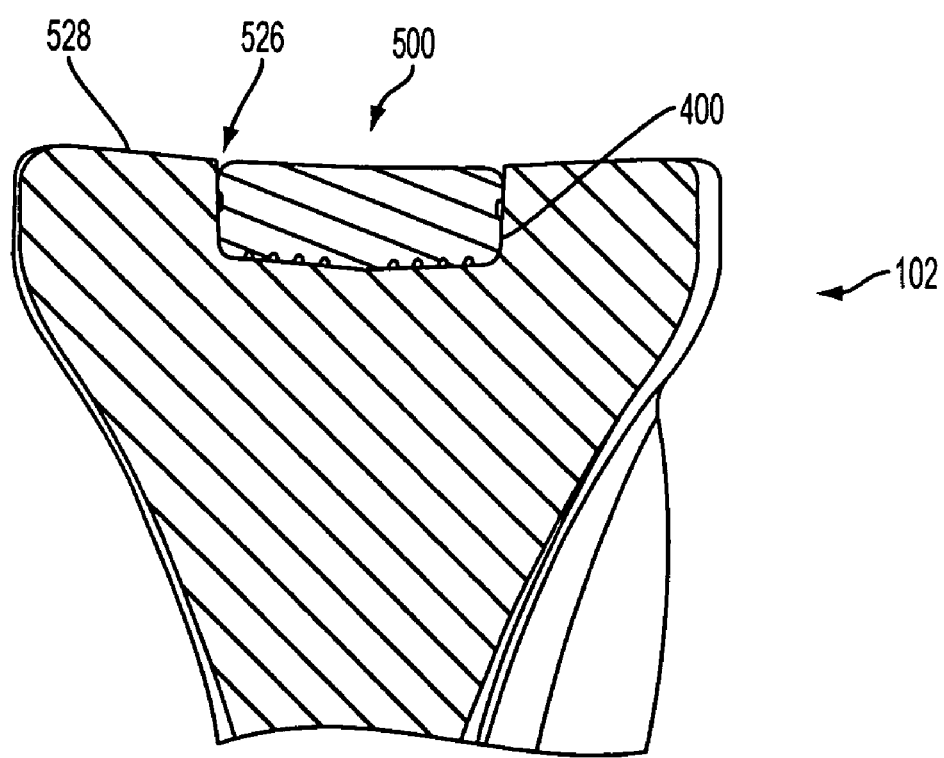
FIG. 14 illustrates a cross-sectional view of a tibia including an articular surface implant.

With reference to FIGS. 12 through 14, an implant 500 is shown that may be used to replace a portion of an articular surface. According to one embodiment flowing from the foregoing description, the implant 500 may be used to replace a portion of a tibial condyle in the context of a uni-compartmental joint replacement. The disclosed implant 500, however, may also suitably be employed for replacing a portion of an articular surface associated with other joints and/or other articular surface replacement procedures. Accordingly, the description herein should not be construed as limiting on the application of the implant 500.

As shown, the implant 500 may be configured as a generally cylindrical member capable of being received in an implant site, e.g. implant site 400, defined by an excised portion of bone disposed on an articular surface, for example created using previously described cutting system 10, drill guide 200, and associated methods. The top surface 512 of the implant 500 may be contoured to generally correspond to a geometry of an articular surface being replaced by the implant 500. Additionally, or alternatively, the top surface 512 of the implant 500 may have a contour generally corresponding to, or complimenting, a geometry of a cooperating articular surface or of an implant provided to replace at least a portion of a cooperating articular surface. As used in any embodiment herein, a contour generally corresponding to a portion of an articular surface being replaced may mean that the contour may provide similar mechanical action in relation to a cooperating articular surfaces, soft tissue, etc during articulation of the joint. Similarly, a contour generally corresponding to a cooperating implant or articular surface shall mean a contour providing smooth cooperating action with respect to such cooperating articular surfaces and/or implants. In any of the foregoing embodiments, the contour of the top surface 512 of the implant 500 may be provided based on quantitative and/or qualitative reference to none, any, all, or any combination of the portion of the articular surface being replaced by the implant 500, the articular surface receiving the implant, the geometry of a cooperating implant, and/or the geometry of a cooperating articular surface.

According to an embodiment, the top peripheral edge 514 of the implant 500 may be relieved. For example, the peripheral edge 514 may be relieved by providing a chamfer or round transition between the top surface 512 and an upper portion of the sidewall 516 of the implant 500. According to one aspect, relieving the peripheral edge 514 in such a manner may reduce the occurrence of a hard edge that may scrape a cooperating implant or articular surface. Relieving the top peripheral edge 514 may accommodate manufacturing or installation tolerances. In a situation in which an edge formed by a projection of the top surface 512 and the upper portion of the sidewall 516 would be slightly recessed or stand slightly proud relative to a surrounding articular surface, the relieved peripheral edge 514 of the implant 500 may still allow smooth movement of a cooperating implant or articular surface across the interface between the surrounding articular surface and the implant 500, notwithstanding such a slight misalignment. As illustrated in FIG. 14 the relieved peripheral edge 514 may produce an indentation or recessed witness 526 around the perimeter of the implant 500 at the interface between the top surface 512 of the implant 500 and the surrounding articular surface 528.

With further reference also to FIG. 13, the bottom surface 518 of the implant 500 may include features to facilitate adhesion between the implant 500 and bone defining an implant site 400, and/or facilitate retention of the implant 500 in the implant site 400. In the illustrated embodiment, the bottom surface 518 is shown including a plurality of concentric grooves, e.g., 520. In a situation in which the implant 500 is to be retained in the implant site 400 using bone cement, the grooves 520 may facilitate adhesion between implant 500 and the implant site by increasing the surface area for adhesive contact. Additionally, or alternatively, the grooves 520 may facilitate retention of the implant 500 in the implant site 400 by providing a mechanical or hydraulic lock between the implant 500 and the bone cement. Further to this aspect, the grooves 520 may be provided at an angle to the axis of the implant 500 to enhance the mechanical lock against removal of the implant 500 along the axis thereof. Similarly, at least some of the grooves 520 may be provided having an undercut portion along at least a portion of the extent thereof. According to still a further aspect, the grooves 520 may allow the implant 500 to be bedded down into a layer of bone cement provided between a bottom of the implant site 400 and the implant 500. Additionally, the grooves 520 may provide a volume for accommodating excess bone cement that may be displaced when the implant is bedded down into a layer bone cement provided between the bottom of the implant site 400 and the implant 500. Various other features may suitably be employed to facilitate and/or enhance adhesion between the implant 500 and an implant site 400, and/or retention of the implant 500 in the implant site 400. For example, the bottom surface 518 of the implant 500 may include a plurality of openings. Similarly, the bottom surface 518 of the implant 500 may include a plurality of intersecting grooves, for example configured in a grid pattern. Various additional and/or alternative features may also be used to facilitate and/or promote adhesion and/or retention of the implant 500.

In a similar manner as the top surface 512, the implant 500 may include a relieved edge 522 between the bottom surface 518 and a lower portion of the side wall 516. As described with respect to the relieved transition of the upper peripheral edge 514, the relieved edge 522 may be provided, for example having, as a chamfer or a rounded over region. The relieved edge 522 may facilitate installation of the implant 500 by allowing a slight initial misalignment between the implant 500 and an implant site 400 into which the implant 500 is being installed. As the implant 500 is installed into the implant site 400 the relieved edge 522 may bear against the articular surface 528 defining the perimeter of the implant site 400 and allow the implant 500 to slide on the relieved edge 522 into proper alignment with the implant site 400. As the implant 500 is further inserted into the implant site 400 the conformance between the cylindrical sidewall 516 and the corresponding circular cross-section implant site 400 may draw the implant 500 into proper alignment with respect to the implant site 400. Furthermore, the relieved edge 522 may provide a volume for accommodating excess bone cement displaced from a central region of the implant site 400 if the implant 500 is bedded down into a layer of bone cement provided between the bottom of the implant site 400 and the implant 500. The relieved edge 522 may also allow the implant 500 to be fully seated in an implant site that may not have a sharp corner between the sidewall and bottom of the implant site.

The side wall 516 of the implant 500 may include one or more circumferential grooves 524. The circumferential groove 524 may provide an additional site for enhanced adhesion and/or mechanical lock between the implant 500 and a sidewall of an implant site 400. For example, bone cement may be applied in the groove 520 and/or to the sidewall of the implant site 400. When the implant 500 is installed in the implant site 400, bone cement may accumulate in the groove 520 and in contact with the side wall of the implant site 400. When the bone cement solidifies a protrusion of bone cement may be formed extending between the side wall of the implant site 400 and the circumferential groove 520 that may resist extraction of the implant 500 from the implant site 400. According to another aspect, the groove 520 may facilitate handling of the implant 500, especially as the implant 500 is inserted through an incision provided for installation of the implant 500, and/or as the implant 500 is installed into the implant site 400. For example, a tool may be provided having features sized to be received in the groove 520 and having a handle to allow manipulation by a clinician. Accordingly, it may be possible to manipulate the implant 500 by tilting the implant 500 as well as translating the implant 500 transversely and axially.

The implant 500 may be provided having features capable of promoting the ingrowth of bone to promote retention of the implant 500 in the implant site 400. For example, the grooves 500 on the bottom surface 518 and/or the circumferential grooves 524 may allow and/or promote the ingrowth of bone. Additional and/or alternative features not illustrated herein may also be provided to promote and/or allow the ingrowth of bone to promote retention of the implant 500 in the implant site 400.

An implant 500 consistent with the present disclosure may be formed from a variety of materials selected for various mechanical, physical, and biological properties. For example, the implant material may be selected to provide at least some degree of shock absorption or cushioning effect. Suitable materials may include various biocompatible polymeric materials, for example, high density polyethylene, ultrahigh molecular weight polyethylene, polyurethane, polyhydroxyethyl methacrylate gel, silicone, polyvinyl alcohol gel, etc. Ceramic material such as alumina or zirconia based materials, as well as various metallic materials, such as stainless steel, titanium, cobalt-chromium alloys, etc, may be used to provide an inherent lubrication or low friction surface. Additionally, the implant 500 may include materials that release or produce therapeutic or lubricating products and may even include biological materials. Numerous other materials provided the foregoing characteristics, and/or other desired characteristics, may be used to produce an implant 500 consistent with the present disclosure.

As alluded to above, the implant 500 may be used in connection with an implant site 400 created using a cutting system 10, drill guide 200 and the associated methods for excising an articular surface to create an implant site 400. As also alluded to, the implant 500 may be installed in the implant site 400 by orienting the implant 500 above the implant site 400 and inserting the implant 500 into the implant site 400 in a generally axial manner.

According to one particular embodiment, the support member 12 may be used to install the implant 500. The implant 500 may be received in the opening 20 of the support 18. The implant 500 may be retained in the opening 20 by a radial pressure applied by the shoe 24, or by the inner shaft received in the lumen of the shaft 16. As described with reference to the cutting operation, installation of the implant 500 may include at least partially opening the joint to facilitate access to the implant site 400 created in an articular surface. The implant 500 may then be delivered to the implant site 400 using the support member 12. The implant 500, retained in the cutter support 18, may be inserted between the cooperating articular surfaces of the femur 100 and tibia 102 and brought into general alignment with the implant site 400. When the implant 500 has been delivered to a desired location, the implant 500 may be released from the support member 12, for example, by withdrawing the translating shaft disposed in the lumen of the shaft 16, and thereby releasing the radial pressure on the implant 500.

Once the implant 500 has been delivered to the implant site, the implant 500 may be pressed into the implant site 400, for example, in part using the circumferential groove 524 for gripping and/or manipulating the implant 500. Bone cement may be applied to the implant 500 and/or the implant site 400. As with the excising operation, installing the implant 500 may be accomplished without damaging or removing the meniscus by retracting the meniscus to one side to expose and provide access to the implant site 400.

The present disclosure also provides a system for replacing a portion of an articular surface extending around a portion of a curvature of the articular surface with an implant. The articular surface replacement system according to this aspect of the disclosure may allow a greater area of an articular surface to be replaced and therein providing a replacement articular surface about a greater range of motion of a joint. Consistent with one embodiment, the system according to this aspect of the disclosure may be used to replace a portion of an articular surface of a femur in a uni-compartmental joint replacement. Consistent with the present system, a relatively large portion of an articular surface may be replaced by an articular surface implant while removing a relatively small mass of articular cartilage, subchondral bone, etc. By removing a relatively small mass of articular cartilage and subchondral bone, the joint may be susceptible to later, more aggressive replacement therapies. Furthermore, a portion of the articular surface may be replaced with a minimum of collateral damage, e.g., to surrounding tissue, ligaments, etc.

The system herein may generally include forming an implant site on the portion of the articular surface to receive the implant. The implant site may generally be formed by a plurality of overlapping excision sites. The system may generally include establishing an axis for each excision site. According to one embodiment, all of the axes may intersect at a common point. The plurality of excision sites may then be formed by excising a portion of the articular surface and subchondral bone extending inwardly from the articular surface along each respective axis. As mentioned above, each of the excision sites may at least partially overlap with an adjacent excision site. The plurality of excision sites may, therefore, provide a generally continuous implant site on the articular surface. An articular surface implant may be installed into the implant site.

Figure 15:
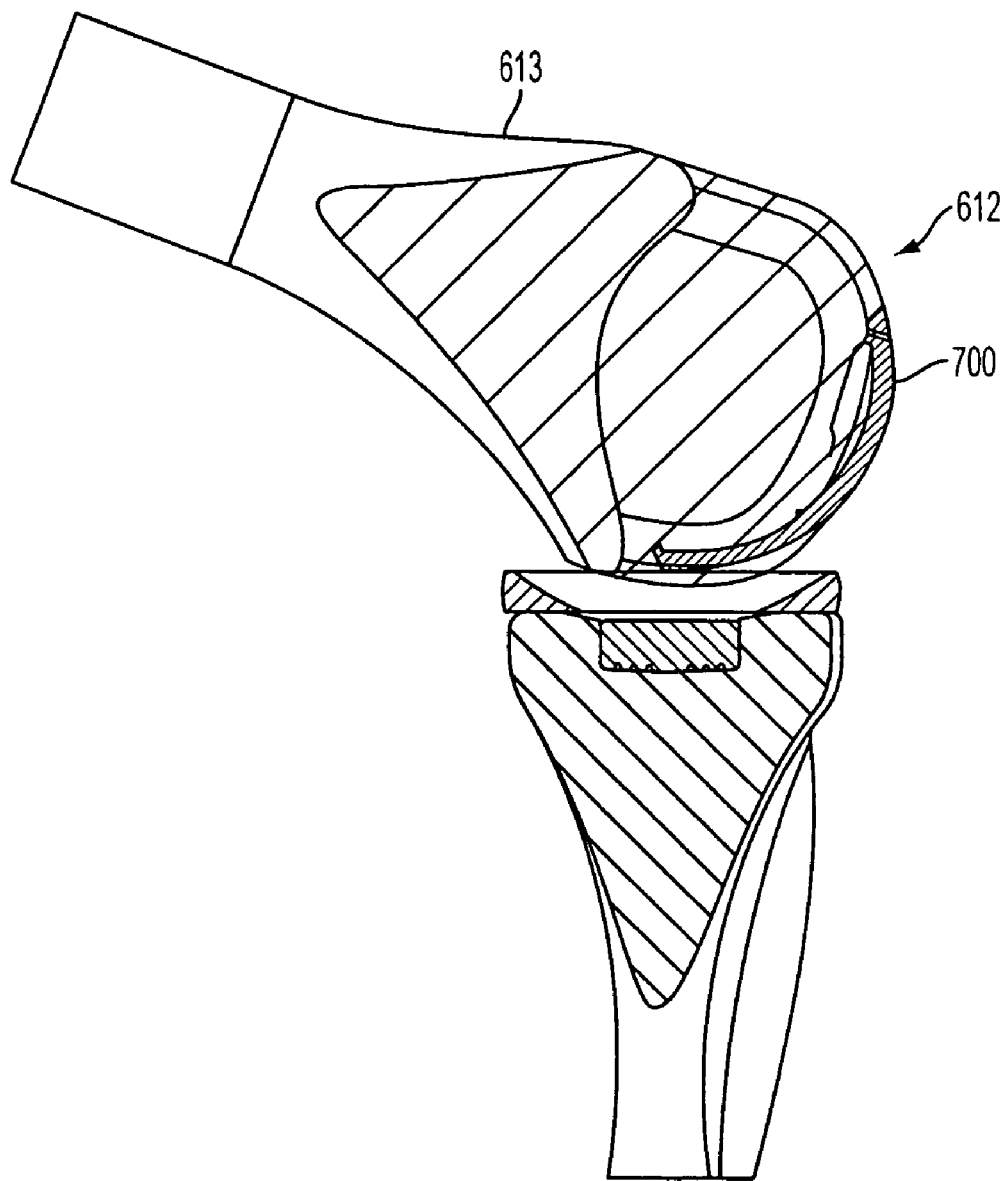
FIG. 15 schematically illustrates a knee joint including an embodiment of a uni-compartmental joint replacement.

Consistent with one embodiment, the system herein may be used to replace a portion of an articular surface of a femur, as during a uni-compartmental knee joint replacement. With reference to FIG. 15, a uni-compartmental joint replacement may include replacing an expanse of the articular surface 612 of the femur 613 extending around a portion of a curvature of a femoral condyle with an articular surface implant 700. Replacing the portion of the articular surface 612 may generally include providing an implant site sized to at least partially receive the implant 700. As stated above, the implant 700 may be received in an implant site including a plurality of at least partially overlapping excision sites. The excision sites may be formed by excising a portion of the articular surface 612 and a portion of the underlying subchondral bone.

Figure 16:
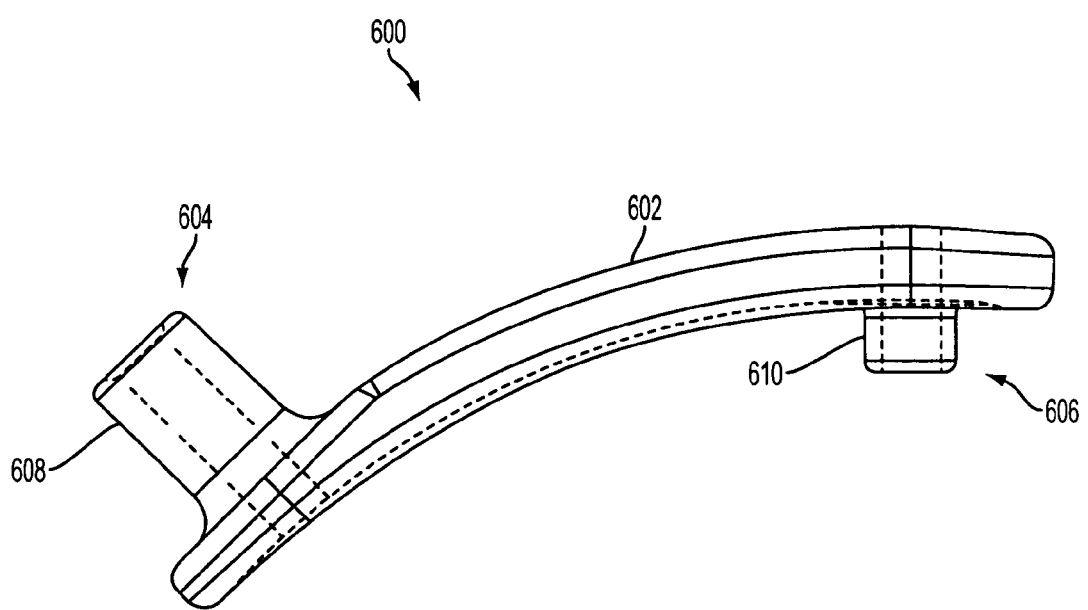
FIG. 16 depicts an embodiment of a drill guide for preparing an implant site on an articular surface.
Figure 17:
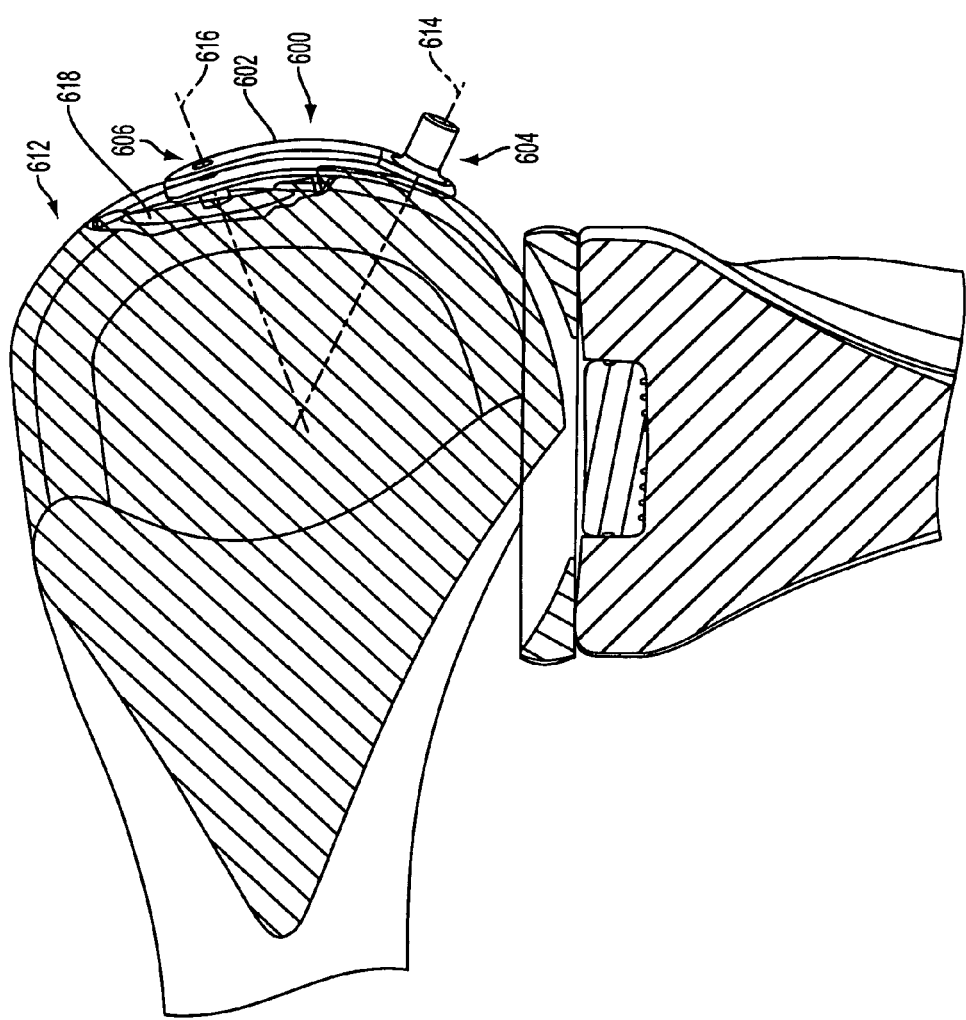
FIG. 17 illustrates the embodiment of a drill guide shown in FIG. 15 positioned on an articular surface.

With reference to FIGS. 16 and 17, a plurality of working axes may be established extending through the articular surface 612. At least one axis may be provided for each excision site to be created to provide the implant site. With particular reference to FIG. 17, a drill guide 600 may be employed to create the plurality of axes having a desired predetermined relationship to one another. The axes may be created extending arcuately around at least a portion of the articular surface 612 of the femur 613.

Referring to FIG. 16, an embodiment of a drill guide 600 that may be used to establish a plurality of axes on an articular surface 612 is shown. The drill guide 600 may generally include a body portion 602 configured to be disposed on an articular surface 612 on which the implant site is to be provided. The drill guide 600 may also include a first and a second drill bushing, generally 604 and 606. The drill bushings 604, 606 may be provided as openings extending through respective bosses 608, 610 extending from the drill guide body 602. The drill bushings 604, 606 may provide the desired alignment and orientation for holes to be drilled into an articular surface as part of the preparation of an implant site.

With further reference to FIG. 17, the drill guide 600 is shown positioned on an articular surface 612 for use in preparing an implant site in the articular surface 612. As shown, the body portion 602 may be an arcuate member that may be shaped to generally conform to the articular surface 612. However, it is not necessary for the body 602 of the drill guide 600 conform to the articular surface 612. For example, the drill guide 600 may only make contact with the articular surface 612 at the drill bushings 604, 606. Alternatively, the drill guide 600 may include contact features spaced from the drill bushings 604, 606 for contacting the articular surface 612 and orienting the drill bushings 604, 606 in a desired relationship relative to the articular surface 612. Variations and modifications in between these two examples may suitably be employed consistent with the present disclosure.

According to one embodiment, a reference axis extending through the articular surface 612 may first be established. According to one embodiment, the reference axis may be provided extending generally normal to the articular surface 612. The reference axis may be established using a normal axis drill guide including a shaft and an aiming feature for projecting a reference axis and a plurality of articular surface contacting features for orienting the axis relative to the articular surface. Such a device is known in the art, for example from U.S. Pat. No. 6,610,067. Other devices may also suitably be used for establishing a reference axis.

In one embodiment, the reference axis may be established in the region of a defect 618 in the articular surface 612, although the reference axis may suitably be provided in locations on the articular surface 612. A guide pin may be inserted into the articular surface 612 along the reference axis, for example by providing a relatively small diameter hole in the articular surface 612 and inserting the guide pin into the hole. A larger hole may then be formed extending along the reference axis. According to one suitable method, the guide pin may be received in a lumen of a cored, or cannulated, drill bit. The cored drill bit may be used to form a pilot hole centered on the guide pin and extending into the articular surface 612.

The drill guide 600, described with reference to FIGS. 16 and 17 may then be used to establish additional working axes through the articular surface 612. Consistent with an embodiment herein, the additional axes established using the drill guide 600 may all intersect at a common point. However, according to alternative embodiments, the several axes established through the articular surface may be oriented parallel to one another, or may be otherwise non-intersecting. Furthermore, two or more of the several axes may intersect at varying points.

According to one embodiment, using the drill guide 600 to establish additional working axes may include installing a location element in the hole produced along the reference axis. The location element may include, for example, a self tapping screw that may be installed in the articular surface 612 or subchondral bone therebeneath. The height of the location element may be adjusted to a predetermined height relative to the articular surface 612. According to one embodiment, adjusting the height of the location element may include mating a positioning insert with the location element and adjusting the location element, as by advancing or retracting the location element within the hole, to position the positioning insert at a predetermined height relative to the articular surface 612, such as tangential with an arc defined by the articular surface 612.

The drill guide 600 may be coordinated with the location element installed through the articular surface 612 so that the drill bushing 606 may be oriented coaxial with the reference axis defined by the location element. For example, a guide rod may be fitted extending from the location element, and the guide rod may be received through a drill bushing, e.g. 606, of the drill guide 600. According to such an embodiment, the guide rod and the location element may be provided having mating features, such as mating precision tapers. The guide rod may, therefore, be aligned along the reference axis. Alternatively, the drill guide 600 and the location element may include cooperating features allowing the drill guide 600 and location element to be coordinated, e.g. aligned, positioned, etc., in a predetermined manner. The boss 610 extending from the drill guide body 602 may bear against, or otherwise interact with, the location element to position the drill guide 600 at a predetermined height relative to the articular surface 612, based on the height of the location element relative to the articular surface 612.

According to a related alternative embodiment, the drill guide 600 may be indexed, or positioned, on the articular surface 612 without the use of a location element. Consistent with one such embodiment, a working axis relative to the articular surface 612 may be established may be established, for example as described above. Also as above, a hole may be drilled into the articular surface 612 generally along the working axis. The boss 610 projecting from the body 602 of the drill guide 600 may be at least partially received in the hole drilled into the articular surface 612. The respective sizes of the hole and the boss 610 may be coordinated to achieve a predetermined tolerance and control the amount of movement, or slop, of the drill guide 600 relative to the articular surface 612. In one embodiment, a snug fit may be achieved between the boss 610 and the hole, thereby restricting movement of the drill guide relative to the articular surface 612.

With the drill guide 600 located relative to the reference axis extending through the articular surface 612, a working axis, or additional axes 614, 616, may be established relative to the articular surface 612. The working axis, or working axes 614, 616, may be established by drilling holes into the articular surface 612 guided by the drill bushing 614. Accordingly, the position and orientation of the working axes 614, 616 may be generally based on reference axis. While the illustrated drill guide 600 only provides two drill bushing 614, 616, additional drill bushings may be provided to allow implant sites of various sized to be formed. Furthermore, consistent with some embodiments, the reference axis used for positioning the drill guide 600 relative to the articular surface 612 may also provide a working axis, e.g., working axis 616.

According to one embodiment, a location element may be installed into each of the holes provided using the drill guide 600. The location elements installed through the articular surface may, therefore, provide a reference, and/or define, the working axes 614, 616 established using the drill guide 600. As used herein, it is not necessary for a location element to extend along the working axis 614, 616 in order for the location element to define the axis. Rather it is only necessary that the location element, or a feature thereof, be oriented in a predetermined relationship to the working axis. Depending upon the initial size of the holes drilled using the drill guide 600, installing a location element may include enlarging the holes to a predetermined size. Enlarging the holes may, in turn, include, for example, installing a guide pin into the holes and drilling over the guide pin using a cored or cannulated drill bit. Other techniques may also suitably be employed consistent with this aspect.

The location elements may include screws, such as self tapping screws. The location elements may be installed having a predetermined depth relative to the articular surface 612. For example, similar to the previously discussed technique, a positioning insert may be associated with the location elements, and the height of the height of the elements may be adjusted to place the positioning insert at a predetermined height relative to the articular surface 612. According to one embodiment, the location elements may include features, such as tapered openings, etc., that may allow cooperating elements and instruments to be placed in a desired position and/or alignment relative to the location element and/or the working axis 614, 616 defined thereby.

Installing location elements in each of the holes provided using the drill guide 600 may be accomplished by articulating the joint to sequentially provide axial access to each of the respective sites. Accordingly, it may not be necessary to separate the joint in order to install an implant on the articular surface 612 of one of the articulating elements. For example, a first site, e.g. a hole in the articular surface 612 drilled along a first axis 616 using the drill guide 600, may be axially access, for example through an incision, by articulating the joint so that the desired site is accessible through the incision. With the first site accessible through the incision, a location element may be installed in the hole. The joint may then be articulated to bring a second site, e.g. a hole in the articular surface 612 drilled along the second axis 614, in to a position whereby the second site may be accessed through the incision. Accordingly, with the second site accessible through the incision a locating element may be installed in the second hole. The process of articulating the joint to permit access to different sites on the articular surface may allow the procedure to be carried out in a minimally invasive manner. That is, rather than providing an incision sufficient to access the entire articular surface at one time, the size of the incision may be reduced. Furthermore, by accessing various portions of the articular surface 612 by positioning the joint in various articulated arrangements, the procedure may be carried out without completely separating the joint. Therefore, the amount of damage to surrounding tissue may be reduced, however, these aspects are not essential within the context of the present disclosure.

Once the working axes 614, 616 have been established, portions of the articular surface 612 and underlying subchondral bone may be excised to provide excision sites. For a first excision site, e.g., along the working axis 616, the joint may be articulated to position the site to permit access as through an incision. With the articular surface 612 positioned to provide access to the site, a portion of the articular surface may be excised. According to one embodiment, the articular surface may be excised using a drill, rotating cutter, or other instrument for excising a generally circular region of the articular surface and/or subchondral bone. Consistent with an embodiment employing a location element associated with each excision site, the location element may include a feature to facilitate locating the excision site and/or controlling the depth of the excision site.

According to a specific embodiment, the location element may include a precision tapered socket. A guide rod having a mating precision taper may be installed into the precision tapered socket. A cutting instrument including a cutting blade configured to rotate around the guide rod may be used to excise a portion of the articular surface 612 and subchondral bone around the working axis 616 to provide a first excision site. For example, a cutting blade, or more than one cutting blades, may be provided extending from a cannulated shaft. The cannulated shaft may be sized to be rotatably received over the guide rod. The first excision site may be provided by rotatably driving the cannulated shaft, and thereby driving the cutting blade or blades, about the guide rod. Consistent with this embodiment, the cutting blade or blades may travel a circular path centered on the working axis 616. As such, the cutting instrument may provide a first excision site defined within the circular path of the cutting instrument and centered on the first working axis 616. In one embodiment, the depth of the excision site may be controlled by providing cooperating features on the cutting instrument and the location element.

For example, the cutting instrument may have a surface that may contact a surface on the location element when the cutting blade, or cutting blades, have achieved a predetermined depth relative to the location element. According to an alternative embodiment, the guide rod and or the cutting instrument may include indicia representative of a cutting depth. According to such an embodiment, the depth of the first excision site may be controlled with reference to such indicia.

Depending upon the diameter of the cutting path defined by the cutting blade or blades, at least a portion of the cutting path defined by the sweep of the cutting instrument may extend outside of the width of the condyle at the excision site. Accordingly, the first excision site may be provided having a truncated circular, or an elongated shape. That is, the first excision site may have a first dimension that may be generally defined by the diameter of the cutting path. The first excision site may also have a second dimension that is generally defined by the width of the condyle within the cutting path at the excised depth.

After the first excision site has been formed, the joint may be articulated to a position allowing a second site may be accessed. According to one embodiment, the joint may be articulated to a position allowing the second site to be accessed through the same incision that was used to access the first site. Similar to the process for forming the first excision site, a second excision site may be formed generally centered on a second working axis 614 by providing a cutting instrument that may be located relative to a second location element. For example, the location element may include a precision taper socket and a guide rod having a precision taper at one end may be received in the precision taper socket of the location element with the guide rod generally extending along the second working axis 614. The cutting instrument may include one or more blades rotatably associated with the guide rod, e.g. via a cannulated shaft of the cutting instrument, such as used to provide the first excision site. The cutting instrument may, therefore, be employed to provide a circular cutting path centered on the second working axis 614. Similar to the process for forming the first excision site, the cutting instrument may be rotatably driven about the guide rod, thereby defining a second excision zone within the circular cutting of the cutting instrument. The depth of the second excision site may be controlled, e.g. by an interaction between the cutting instrument and the location element, by reference to indicia on the cutting instrument and/or the guide rod, etc.

Also similar to the first excision site, according to one embodiment, at least a portion of the cutting path or excision region defined by the sweep of the cutting instrument may extend outside of the width of the condyle. Accordingly, the second excision site may be provided having a truncated circular or elongated shape having a dimension defined by the diameter of the cutting path and a second dimension defined by the width of the condyle within the cutting path at the excised depth.

Consistent with the system according to the present disclosure, the cutting paths defining the first and second excision sites may intersect, or at least partially overlap one another. The intersection or partial over lapping of the first and second excision sites may provide a generally continuous excised region. The continuous excised region may at least partially define an implant site in the articular surface 612. According to one embodiment, the first and second excision sites may overlap to a degree wherein one dimension of the continuous excised region may be generally defined by the width of the condyle at the excised depth.

The general procedure of forming an excision site using a cutter having a circular cutting path centered about a working axis defined, e.g., by the drill guide 600, may be carried as many times as necessary to create an implant site having the desired size, shape, and expanse. As with the first and second excision sites, each excision site may intersect, or at least partially overlap adjacent excision sites. The plurality of excision sites may, therefore, provide an implant site that includes a plurality of individual excision sites. As with the first and the second excision sites, at least a portion of the cutting path defining any of the additional excision sites may extend outside of the width of the condyle, thereby providing truncated circular, or an elongated, excision sites, in which one dimension of the excision site may be defined by the width of the condyle within the cutting path at the excised depth.

Consistent with an alternative embodiment, the plurality of intersecting, or at least partially overlapping, excision sites may be formed without the use of location features. According to one such embodiment, a plurality of working axes 614, 616 extending through the articular surface 612 may be defined, for example using the drill guide 600. The plurality of working axes 614, 616 may be defined, e.g., by holes drilled into the articular surface 612 with the aid of the drill guide 600. According to one embodiment, a guide pin, or guide rod, may be inserted into each of the holes and extending along the respective working axes 614, 616. A cutting instrument, as described with respect to the foregoing embodiments, may be used in combination with the guide pins, or guide rods, associated with each working axis 614, 616 to excise a portion of the articular surface 612 and underlying subchondral bone. This method may differ generally only by the omission of location elements. In a similar embodiment, rather than providing guide pins, or guide rods, associated with each of the working axes 614, 616, a cutting instrument may be provided including a pin or rod and one or more cutting blades associated therewith. The pin or rod may be sized to be received in the holes in the articular surface 612 provided using the drill guide 600. An excision site may be formed by inserted a distal end of the pin or rod in a hole associated with a working axis 614, or 616 and rotating the cutting instrument with in the hole. Consistent with such an embodiment, the hole in the articular surface may serve as a bushing for the cutting instrument.

An implant may be installed in the implant site at least partially defined by the plurality of intersection or at least partially overlapping excision sites. Accordingly, the implant may replace at least a portion of the articular surface 612. In one embodiment, one or more of the location elements may be retained in the subchondral bone after the excision sites have been formed. The location elements may, therefore, be used as fixation elements for retaining the implant in position in the implant site. For example, in an embodiment in which the location elements include precision tapered socket, the implant may include a fixation feature including a precision tapered post that may be sized to be received in a precision tapered socket of the location element. The tapered post fixation feature of the implant may be pressed into the tapered socket to provide a secure frictional engagement therebetween. Alternative methods and features may also, or alternatively, be used for securing an implant in an implant site.

Figure 18:
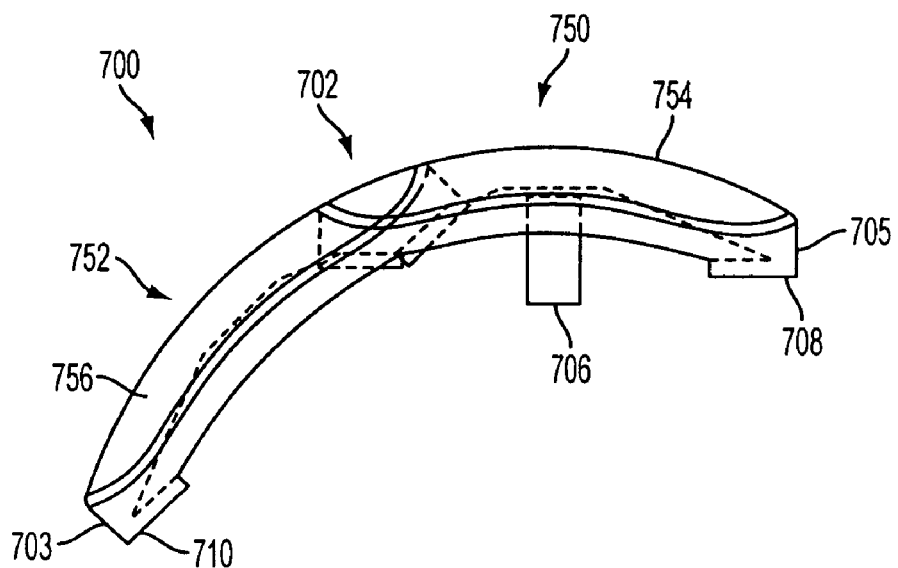
FIG. 18 is a side elevation schematic drawing depicting an implant provided by two overlapping implants.
Figure 19:
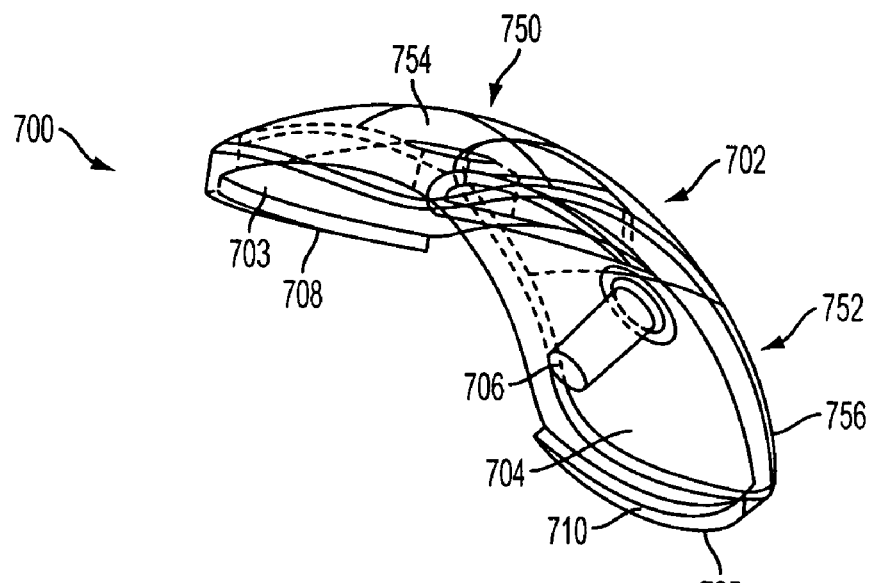
FIG. 19 is an underside perspective schematic drawing of implant shown in FIG. 18.
Figure 20:
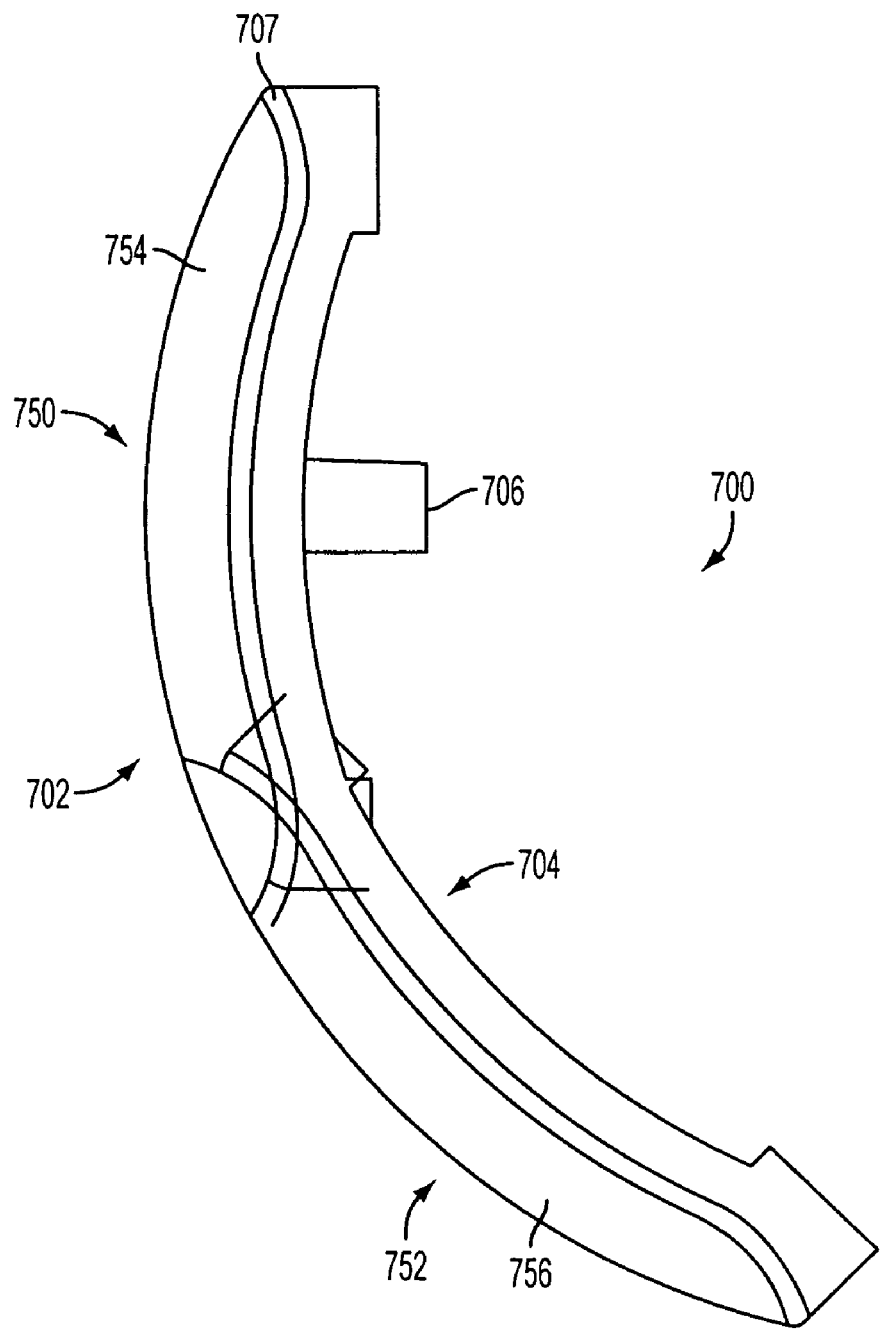
FIG. 20 is an side elevation view of the implant shown in FIG. 18.
Figure 21:
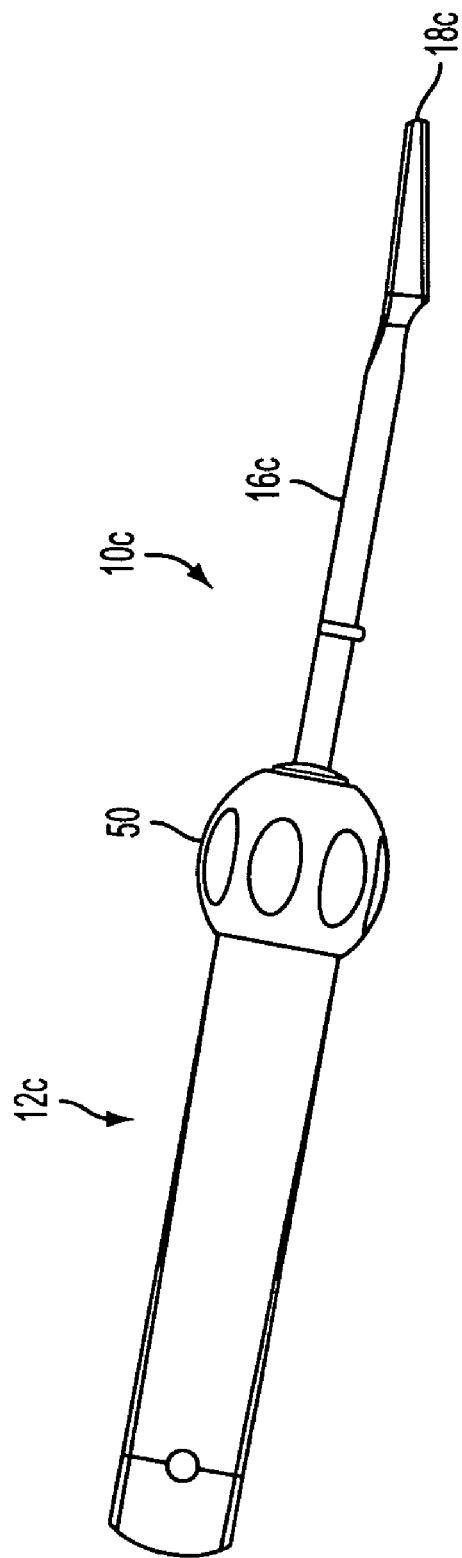
FIG. 21 is a perspective view of an embodiment of a low profile cutting system consistent with the present disclosure.

Turning to FIGS. 18 through 20, an embodiment of an implant 700 that may be used to replace a portion of an articular surface is illustrated in a variety of views. The implant 700 may be used to replace a portion of an articular surface, for example, extending around a portion of the curvature of a femoral condyle in a knee joint, as in a unicompartmental knee replacement. An implant 700 consistent with this aspect of the disclosure may also suitably be used for replacing articular surfaces associated with other joints and/or other articular surface replacement procedures. Accordingly, the description herein should not be construed as limiting the application of the implant 700.

As shown, an embodiment of the implant 700 may generally include a top, or bearing, surface, generally indicated at 702, and a bottom, or bone facing, surface, generally indicated at 704. The bearing surface 702 may be a surface that may replace a portion of an articular surface receiving the implant 700. As such, the bearing surface 702 may generally face a cooperating articular surface and/or an implant disposed in or a cooperating articular surface. The bone facing surface 704 may face the bone underlying the articular surface being replaced by the implant 700. In some embodiments herein, the bone facing surface 704 may be at least partially received in an implant site.

In the context of an implant suitable for replacing a portion of the articular surface of a femoral condyle in a uni-compartmental knee replacement, the arcuate expanse of the bearing surface 702 may be such that a portion of the bearing surface may be tangential with a first plane, and another portion of the bearing surface may be tangential with a second plane that is generally perpendicular to the first plane. The arcuate expanse of the bearing surface 702, however, may be varied to suit specific applications, and the foregoing description should not be construed as limiting on the scope of the implant 700 herein. Similarly, in context of an implant for replacing a portion of an articular surface of a femoral condyle, the implant 700 may have a width that may generally be defined by the width of the articular surface of the condyle. Accordingly, an embodiment of the implant 700 may generally have an oblong shape from the perspective of the bearing surface 702 in plan view. As such, the implant 700 may include rounded end regions 703, 705 generally. The sides extending between the end regions 703, 705 may be generally linear, or may be arcuate having a radius larger than the radius of the rounded end regions 703, 705.

According to one embodiment herein, at least a portion of the perimeter edge of the bearing surface 702 may be relieved and not present a hard edge. For example, at least a portion of the perimeter edge of the bearing surface 702 may be chamfered or rounded, for example as indicated at 707 in FIG. 20. When the implant 700 is installed in an articular surface, the relieved configuration of the perimeter edge of the bearing surface 702 may provide a slight recess or witness line between the bearing surface 702 of the implant 700 and the surrounding articular surface. The relieved perimeter edge of the bearing surface 702 may facilitate smooth movement of a cooperating articular surface, implant, etc. across the transition between the surrounding articular surface and the implant 700. For example, the relieved perimeter edge may accommodate a slight difference in height of the implant 700 relative to the surrounding articular surface by not providing a hard edge that may scrape, abrade, or wear an interacting surface.

As best seen in the schematic illustrations of FIG. 19, the implant 700 may include a lip 708, 710 on one, or both, ends 703, 705 of the implant 700. When the implant 700 is installed into an implant site in an articular surface, the lips 708, 710 may cut into a portion of the articular surface and/or subchondral bone surrounding the adjacent regions of the implant site. Accordingly, fraying and/or further deterioration of articular cartilage surrounding the implant site may be reduced or eliminated.

The implant 700 may also include one ore more fixation features 706. The fixation feature 706 may facilitate securing the implant 700 in a desired position in an implant site. Consistent with the illustrated embodiment, the fixation feature 706 may be provided as protruding feature. According to one example, the fixation feature 706 may be provided as a precision taper. The precision taper may be adapted to be at least partially received in a mating precision taper or a cylindrical opening in a fixation element disposed in bone underlying the articular surface. For example a screw may provide a fixation element that may be disposed in the bone underlying the articular surface. The screw may include a central bore that is adapted to receive the fixation feature 706 of the implant 700.

According to alternative embodiments, the fixation feature 706 of the implant may include structures such as a barbed protrusion that may be pressed into a hole formed in the bone underlying the articular surface. The fixation feature 706 may be pressed into the hole and the barbed elements of the protrusion may engage the bone defining the wall of the hole. The engagement between the bone and the barbed elements may resist extraction of the implant 700 from the articular surface. In a similar embodiment, the fixation feature 706 may include a post having protrusion and/or indentations thereon. The implant 700 may be secured in a desired location by cementing the post into a hole formed in the bone underlying the articular surface. The protrusions and/or indentations may facilitate mechanical lock between bone cement and the fixation feature 706 of the implant 700. Various other structures, protrusions, receptacles, etc., may be used for securing the implant 700 in a desired location.

Consistent with an embodiment of the present disclosure, the implant 700 may be configured to have a bearing surface 702 that may approximate the geometry or curvature of the articular surface being replaced by the implant 700. In one embodiment the geometry of the load bearing surface may be based on the actual articular surface being replaced. For example, mapping techniques known in the art may be used to measure the actual geometry of the region of the articular surface being replaced. An implant 700 may then be constructed or selected from a set of implants having predetermined geometries to at least generally conform to mapped or measured geometry of the articular surface being replaced. Alternatively, an implant 700 for a specific application may be fabricated or selected from a set of standard sized/shaped implants to provide a general approximation of the articular surface being replaced. Selection or fabrication of an implant 700 may rely on various degrees of quantitative reference to the articular surface being replaced, including no quantitative reference to the articular surface.

Consistent with an alternative embodiment, the implant 700 may be configured to provide smooth interaction with a cooperating implant on a cooperating articular surface. Accordingly, the cooperating implant may not have a geometry approximating the geometry of the cooperating articular surface. In such a situation, rather than providing the implant 700 having a geometry approximating the articular surface being replaced, the implant 700 may have a contour or geometry that is configured to provide smooth interaction with the cooperating implant. In one such embodiment, the implant 700 and the cooperating implant may be provided as a pair and/or be provided having coordinated geometries selected to provide a desired, e.g., smooth, interaction with one another in an application in a particular joint or in general.

The schematic illustrations in FIGS. 18 through 20 show an embodiment of a design methodology for an implant 700 is schematically illustrated. Consistent with the schematic depictions, the implant 700 may include a plurality of overlapping implant portions 750 and 752 having a truncated circular or oblong configuration. Each of the overlapping implant portions 750, 752 making up the implant 700 may generally correspond to respective excision sites making up the implant site. As such, the overlapping implant portions 750 and 752 may be arranged in an angularly and/or radially displaced configuration that may generally correspond to the angular and/or radial displacement of the respective excision sites. Also similarly, the implant portions 750, 752 may each be oriented relative to a respective axis utilized to form the respective excision sites, although other configurations are contemplated herein.

It should be noted that the overlapping implant portions 750, 752 need not exist as separate, discrete components, but may rather provided as a single unitary implant 700. Consistent with an alternative embodiment, the individual implant portions may be provided as separate components that may be assembled and/or arranged in the implant site to provide a generally continuous implant. When the bearing surfaces 754, 756 of the implant portions are faired, or lofted, to provide a smooth continuous surface, an implant 700 may be provided having a continuous bearing surface that may generally represent an original articular surface being replaced and/or provide smooth interaction about the range of motion of the implant 700 with a cooperating articular surface and/or cooperating implant.

Consistent with the previously described system for providing an implant site, each of the implant portions 750, 752 may have a shape, as viewed looking at the bearing surface 754, 756 of the implant, which may generally correspond to a shape of a respective excision site making up the implant site on the articular surface 612. In one embodiment the geometry of the load bearing surface 754, 756 of each implant portion 750, 752 may be based on the actual articular surface being replaced at each excision site. For example, mapping techniques known in the art may be used to measure the geometry of the actual articular surface being replaced in the region of the respective excision sites. The implant portions 750, 752 may have predetermined geometries to at least generally conform to a mapped or measured geometry of the articular surface being replaced in the region of each excision site. Alternatively, the implant portions may have a standard size/shape providing a general approximation of the articular surface being replaced. The geometry or contour of the implant portions 750, 752 may rely on various degrees of quantitative reference to the regions of the articular surface being replaced, including no quantitative reference to the articular surface.

Consistent with the foregoing, the implant portions 750, 752 may each be a truncated circular or oblong member, when viewed in plan view from the bearing surfaces 754, 756. By truncated circular or oblong it is meant that the implant portions 750, 752 may be derived, for example, from a circular implant having a diameter greater than the width of a condyle intended to receive the implant 700. The width of the implant, for example across the medial-lateral plane of the condyle, may be less than the length, i.e., along the anterior-posterior plane of the condyle. Accordingly, a circular implant may be truncated in the medial-lateral plane to have a width that is equal to the width of the condyle at the implant site. Alternatively, one or more of the implant portions 750, 752 may include a width, e.g., across the medial-lateral plane condyle, that is greater than the length of the implant portions 750, 752, e.g., along the anterior-posterior plane of the condyle. This situation may occur if the curvature of a condyle in the anterior-posterior plane is such that, for an implant having a desired thickness, the articular surface curves away from the excision site in the anterior-posterior plane in a smaller dimension than the width of the condyle. Accordingly, the implant portions 750, 752 may be truncated in the anterior-posterior plane. Further embodiments contemplate a truncated circular implant wherein the implant is truncated in a plane oriented at an angle to the anterior-posterior and medial-lateral planes. Additionally, it is contemplated herein that the truncated implant may be asymmetrical.

In addition to having a shape that may correspond to an excision site on an articular surface, the implant portions 750, 752 may overlap one another to the same degree that the respective excision sites overlap one another to form the implant site. Accordingly, the shape of an implant 700 composed of the implant portions 750, 752 may generally conform to an implant site including a plurality of excision sites.

While the illustrated implant 700 may be conceptually thought of as two angularly and/or radially displaced, overlapping truncated circular implant portions 750, 752, an implant accommodating a larger expanse may be conceptually provided by more than two overlapping truncated circular implant portions, each arranged angularly and/or radially displaced from one another. Similarly, various bearing surface contours may be developed, again conceptually, by providing a plurality of truncated circular or oblong implants of varying sizes and arranged at varying angular and/or radial displacements relative to the other truncated circular or oblong implant portions and corresponding to respective overlapping excision sites.

The foregoing design methodology may provide an implant 700 that may include an implant portion 750, 752 corresponding to each excision site in the articular surface formed to provide the implant site. Accordingly, the implant 700 may not only have a bearing surface that may approximate the geometry or contour of the portion of the original articular surface 612 being replaced, but the implant 700 may also include a bone facing surface 704 having a geometry that is adapted to be received in the implant site formed by a plurality of individual excision sites.

The foregoing disclosure relates to one possible conceptual methodology for designing an implant herein. However, various alternative design methodologies may also suitably be employed for designing an implant consistent with the present disclosure. Furthermore, the implant should not be considered to be limited by any particular design methodology by which such an implant is obtained. Accordingly, the disclosed embodiment of a design methodology for achieving an implant herein should not be construed as limiting the actual implant as disclosed.

Consistent with the foregoing design methodology, an implant 700 may be provided having a bearing surface approximating an articular surface to be replaced, each of the overlapping implant portions 750, 752 may be provided having a load bearing surface 754, 756 that may approximate the geometry or curvature of a region of the articular surface to be replaced by the respective regions of the implant 700 associated with each of the overlapping implant portions 750, 752. The geometry or curvature of the overlapping implant portions 750, 752 may be based on the articular surface being replaced, e.g. based on data collected using measuring or mapping techniques. Alternatively, the geometry or contour of the overlapping implant portions 750, 752 may be provided based on a general approximation of the respective regions of the articular surface being replaced. Herein, approximating the articular surface being replaced, and/or providing a bearing surface based on the articular surface being replaced, may rely on various degrees or quantitative reference to the articular surface being replaced, including no quantitative reference to the articular surface.

An implant 700 consistent with the present disclosure may be formed from any suitable biocompatible material. For example, an implant 700 may be formed, in whole or in part, from a metal or metal alloy, e.g. Co—Cr—W—Ni, Co—Cr—M, Co—Cr alloys, Co—Cr-Molybdenum alloys, Cr—Ni—Mn alloys, powder metal alloys, stainless steel, titanium and titanium alloys. Ceramic materials, such as aluminum oxide or zirconium oxide, may also suitably be used to form an implant herein. Polymeric materials may also be used to produce implant according to the present disclosure. For example, polyurethanes, polyethylene, ultra-high molecular weight polyethylene, thermoplastic elastomers, biomaterials such as polycaprolactone may all be used herein. Additionally, implants herein may be produced from diffusion hardened materials, such as Ti-13-13, Zirconium and Niobium. Coatings, or coated materials, may be employed to provide porous surfaces, e.g., on bone-contacting surfaces, hydrophilic surfaces, e.g., on load bearing surfaces. Furthermore, the present disclosure contemplates the use of composite implants that may include more than one material and/or may include more than one type of materials, for example, a metal or metal alloy and a polymeric material. Consistent with this last aspect, composite implants are contemplated herein that may include load bearing and/or bone facing surfaces that may include more than one material and/or more than one type of material.

What is claimed is:

1. An implant for replacing a portion of an articular surface comprising:
  a first implant portion defining a first end region of said implant, said first implant portion comprising:
    a first load bearing surface having a geometry generally corresponding to the original contour of a first portion of said articular surface being replaced, wherein said first portion of said articular surface is centered around a first axis extending outwardly from said articular surface;
    a first bone facing surface having an overall non-planar geometry which is revolved around said first axis such that said first bone facing surface is generally radially symmetrical about said first axis; and
    a fixation feature extending outwardly from said first bone facing surface along said first axis; and
  at least a second implant portion comprising:
    a second load bearing surface having a geometry generally corresponding to the original contour of a second portion of said articular surface being replaced, wherein said second portion of said articular surface is centered around a second axis extending outwardly from said articular surface; and
    a second bone facing surface having an overall non-planar geometry which is revolved around said second axis such that said second bone facing surface is generally radially symmetrical about said second axis,
  wherein said first and said second implant portions partially overlap.

2. An implant according to claim 1, wherein said first implant portion and said second implant portion are integrally formed.

3. An implant according to claim 1, wherein said geometry of said first and second implant portions are based on a measured contour of a recipient's articular surface.

4. An implant according to claim 1, wherein said bone facing surface is capable of being at least partially received in an implant site formed in said articular surface.

5. An implant according to claim 1 wherein said fixation feature comprises a tapered post configured to be received in a corresponding tapered opening of a screw.

6. An implant according to claim 1, wherein said first implant portion is tangential to a first plane and said second implant portion is tangential to a second plane, said first plane and said second plane being perpendicular to one another.

7. The implant of claim 1, wherein said first implant portion comprises a surface contour based on an intersection of a first portion of an articular surface and a first circular projection having a first diameter and wherein said second implant portion comprises a surface contour based on an intersection of a second portion of said articular surface and a second circular projection having a second diameter.

8. The implant according to claim 7, wherein a length of at least one of said first and said second diameters is greater than a width of an overlapping region of said first and said second implant portions.

9. The implant according to claim 7, wherein said width of an overlapping region of said first and said second implant portions is defined by a maximum width of said articular surface at said intersections of said articular surface and said first and said second circular projections.

10. The implant of claim 7, wherein said first implant portion defines a first rounded end region of said implant having said first diameter based on said first circular projection.

11. The implant of claim 10, wherein said second implant portion defines a second rounded end region of said implant having said second diameter based on said second circular projection.

12. The implant of claim 7, wherein said first implant portion defines a first truncated circular geometry.

13. The implant of claim 12, wherein said second implant portion defines a second truncated circular geometry.

14. The implant according to claim 13, wherein said first and said second truncated circular geometries have substantially the same diameter.

15. The implant according to claim 13, wherein said first and said second truncated circular geometries have different diameters.

16. The implant of claim 1, wherein said load bearing portion further comprises at least a third implant portion partially overlapping with said at least a second implant portion.

17. The implant of claim 16, wherein said third implant portion defines a second end region of said implant.

18. The implant of claim 1, wherein said first and said second load bearing surfaces are configured to be flush with said articular surface when said implant is received in an implant site formed in said articular surface.

19. An implant for replacing a portion of an articular surface comprising:
  a first implant portion defining a first end region of said implant, said first implant portion comprising:
    a first load bearing surface having a geometry generally corresponding to the original contour of a first portion of said articular surface being replaced, wherein said first portion of said articular surface is defined by a first radius centered around a first axis extending outwardly from said articular surface;
    a first bone facing surface having an overall non-planar geometry which is revolved around said first axis such that said first bone facing surface is generally radially symmetrical about said first axis; and
    a fixation feature extending outwardly from said first bone facing surface along said first axis; and at least a second implant portion comprising:
- a second load bearing surface having a geometry generally corresponding to the original contour of a second portion of said articular surface being replaced, wherein said second portion of said articular surface is defined by a second radius centered around a second axis extending outwardly from said articular surface; and
- a second bone facing surface having an overall non-planar geometry which is revolved around said second axis such that said second bone facing surface is generally radially symmetrical about said second axis, wherein said first and said second implant portions partially overlap; and wherein said first and said second load bearing surfaces are generally flush with said articular surface surrounding said first and said second excision sites, respectively.

20. The implant of claim 19, wherein said first radius and said second radius are different.

21. The implant of claim 19, wherein said fixation feature comprises a tapered post.

* * * * *